US009931488B2

(12) United States Patent
Bunch et al.

(10) Patent No.: US 9,931,488 B2
(45) Date of Patent: Apr. 3, 2018

(54) HOLDING DEVICES FOR ELONGATED INSTRUMENTS

(71) Applicant: EPGEAR, LLC, Draper, UT (US)

(72) Inventors: Thomas Jared Bunch, South Jordan, UT (US); Troy J. Orr, Draper, UT (US)

(73) Assignee: EPGEAR, LLC, Draper, UT (US)

( * ) Notice: Subject to any disclaimer, the term of this patent is extended or adjusted under 35 U.S.C. 154(b) by 355 days.

(21) Appl. No.: 14/565,326

(22) Filed: Dec. 9, 2014

(65) Prior Publication Data

US 2015/0157829 A1 Jun. 11, 2015

Related U.S. Application Data

(60) Provisional application No. 61/913,898, filed on Dec. 9, 2013.

(51) Int. Cl.
*A61M 5/32* (2006.01)
*A61M 25/02* (2006.01)
*A61M 25/09* (2006.01)

(52) U.S. Cl.
CPC ........ *A61M 25/02* (2013.01); *A61M 2025/024* (2013.01); *A61M 2025/028* (2013.01); *A61M 2025/09125* (2013.01)

(58) Field of Classification Search
CPC .... A61M 25/02; A61M 39/284; A61M 39/28; A61M 39/286; A61M 5/1418
USPC ................................................. 604/174, 250
See application file for complete search history.

(56) References Cited

U.S. PATENT DOCUMENTS

| 4,417,710 A | 11/1983 | Adair |
| 5,010,899 A | 4/1991 | Thompson |
| 6,113,062 A * | 9/2000 | Schnell ............... A61M 39/284 251/10 |
| 6,314,959 B1 | 11/2001 | Griesbach et al. |
| 6,629,615 B2 | 10/2003 | Kim |
| 7,234,677 B2 * | 6/2007 | Zerfas ................. A61M 39/284 251/10 |
| 7,770,583 B2 | 8/2010 | Harris et al. |
| 8,342,459 B2 | 1/2013 | Garrison et al. |
| 8,523,824 B2 | 9/2013 | Teirstein et al. |
| 2009/0223041 A1 | 9/2009 | Garrison et al. |

OTHER PUBLICATIONS

Progressive Dynamics Medical, Cord Companion™ Instructions for Use, publication date unknown, available at http://www.progressivedynamicsmedical.com/pdf/cc_duo_usage_instructions.pdf, last visited Apr. 15, 2016 (2 pages).

(Continued)

*Primary Examiner* — Phillip Gray
(74) *Attorney, Agent, or Firm* — Stoel Rives LLP

(57) ABSTRACT

A holding device for elongated instruments can include a channel for receiving therein an intermediate portion of an elongated instrument. The holding device can include a lock that includes a seat against which the elongated instrument can rest and a resiliently deformable retention arm that is movable relative to the seat. The lock, when in the securing state, can retain within the channel the intermediate portion of the elongated instrument to prevent the intermediate portion from one or more of translating or rotating relative to the device.

23 Claims, 17 Drawing Sheets

(56) References Cited

OTHER PUBLICATIONS

Vascular Disease Management, Vascular Solutions launches the Angio Assist™ Docking Station and the Teirstein Edge™ Device Organizer, Nov. 8, 2010, available at http://www.vasculardiseasemanagement.com/content/vascular-solutions-launches-angio-assist%E2%84%A2-docking-station-and-teirstein-edge%E2%84%A2-device-organiz, last visited Apr. 15, 2016 (4 pages).

Vascular Solutions, Teirstein Edge™ Device Organizer Instructions for Use, Feb. 2013 (1 page).

Vascular Solutions, Teirstein Edge™ Device Organizer Instructions for Use, Dec. 2015 (1 page).

\* cited by examiner

HOLDING DEVICES FOR ELONGATED INSTRUMENTS

CROSS-REFERENCE TO RELATED APPLICATIONS

This application claims the benefit under 35 U.S.C. § 119(e) of U.S. Provisional Patent Application No. 61/913,898, titled HOLDING DEVICES FOR ELONGATED INSTRUMENTS, which was filed on Dec. 9, 2013, the entire contents of which are hereby incorporated by reference herein.

BACKGROUND

Various medical procedures involve insertion of one or more catheters and/or other elongated instruments in a patient. For example, in some cardiac procedures, a plurality of catheters may be introduced into one or more blood vessels. Embodiments discussed below can be used in such contexts, and represent advancements over known techniques relative to the elongated instruments. However, the present disclosure is not necessarily limited to such procedures.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Figure 1A:
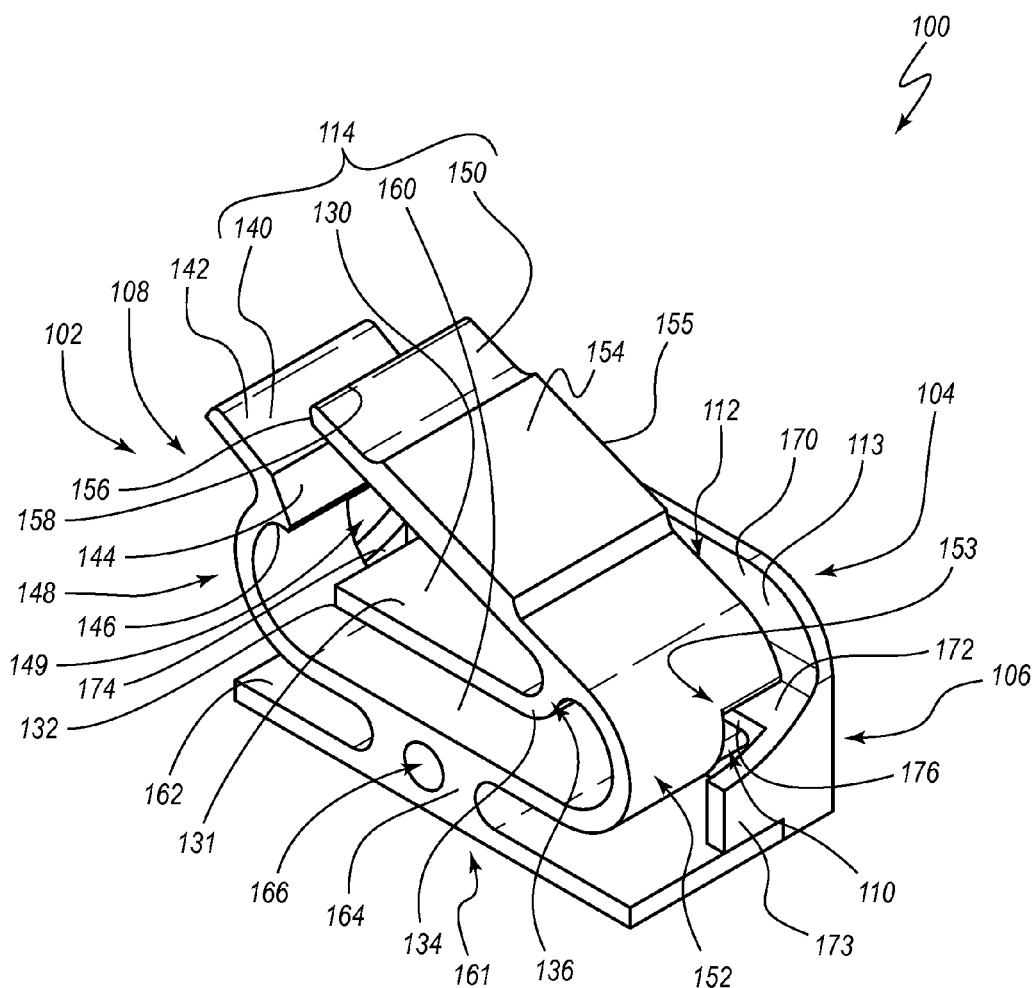
FIG. 1A is a perspective view of an embodiment of a holding device in an open state.

Various medical procedures involve the use of one or more elongated instruments. As used herein the term "elongated instrument" is directed to devices such as catheters (e.g., ablation catheters, electrogram catheters, diagnostic catheters, sensing catheters, temporary pacemaking catheters), cannulae, guidewires, sensor wires, electrical cables, tubes, support lines, etc. Such elongated instruments can include a distal end and a proximal end. In some arrangements, the distal end of an elongated medical instrument, such as a catheter, can be introduced into the patient in any suitable manner, such as, for example, via a sheath introducer and accompanying techniques. The elongated instrument may, for example, be said to enter the patient at an insertion site. In some instances, multiple catheters may enter a patient at a single insertion site. In other or further instances, multiple insertion sites are used for multiple catheters. The distal end of the elongated instrument may be advanced to a desired position within the patient. In some instances, it can be desirable to prevent the elongated instrument from moving longitudinally, or stated otherwise, from translating along a longitudinal axis thereof, once the distal end has been positioned as desired. Preventing such longitudinal movement of the elongated instrument relative to the insertion site of the patient can maintain the distal end of the elongated instrument at the desired position within the patient. Further, in some instances, a proximal portion of the elongated instrument may be rotated or otherwise manipulated while the distal end is advanced to the desired position. Such rotation and/or other manipulation may give rise to a torque about the longitudinal axis of the elongated instrument. It can further be desirable to maintain the torque at the proximal region of the elongated instrument to maintain the distal end in a desired orientation within the patient.

By way of non-limiting examples, in various instances, one or more catheters may be inserted into a patient in electrophysiology or cardiology procedures. In certain of such procedures, one or more of an electrogram-detecting catheter, a mapping catheter, a diagnostic catheter, or an ablation catheter may be introduced into a patient. In some instances, multiple catheters are simultaneously within the patient. In some instances, a practitioner may advance the distal end of a catheter to a desired position within the patient by manipulating (e.g., via a hand) more proximal regions of the catheter at an exterior of the patient. The practitioner may continue to hold the proximal region of the catheter, such as between a thumb and one or more fingers, once the distal end of the catheter is at a desired position. This method of preventing translational and/or rotational movement of the catheter can, in some instances, monopolize a hand of the practitioner that might otherwise be used advantageously elsewhere in the procedure. Moreover, the positioning and use of multiple catheters can be complicated by the need or desire to prevent each catheter that is placed from moving from a desired orientation.

In other or further instances, many critical care patients may have one or more sensor wires, fluid tubes, and/or support lines running to and from support equipment used in caring for the patient. Such elongated instruments may be coupled with sensors, needle-free access ports, and/or other devices positioned on or near the patient at a distal end thereof, and coupled with an intravenous reservoir, sensor, monitor, or other suitable device at a proximal end thereof. In some instances, various elongated instruments may be become tangled or otherwise difficult to manage, such as when the patient changes position. In some situations, the elongated instruments may be inadvertently disconnected from the support equipment and/or the patient, which could result in undesired consequences. Certain embodiments discussed herein may be advantageously used in such contexts.

Embodiments disclosed herein can be used in contexts such as those described above and may ameliorate or resolve one or more of the foregoing drawbacks and/or one or more other drawbacks not mentioned above. Such improvements will be evident from the discussion that follows. It is also noted that the advantages and uses of various embodiments are not necessarily limited to the procedures just mentioned. For example, embodiments disclosed herein may be used in contexts other than medical procedures.

Figure 1B:
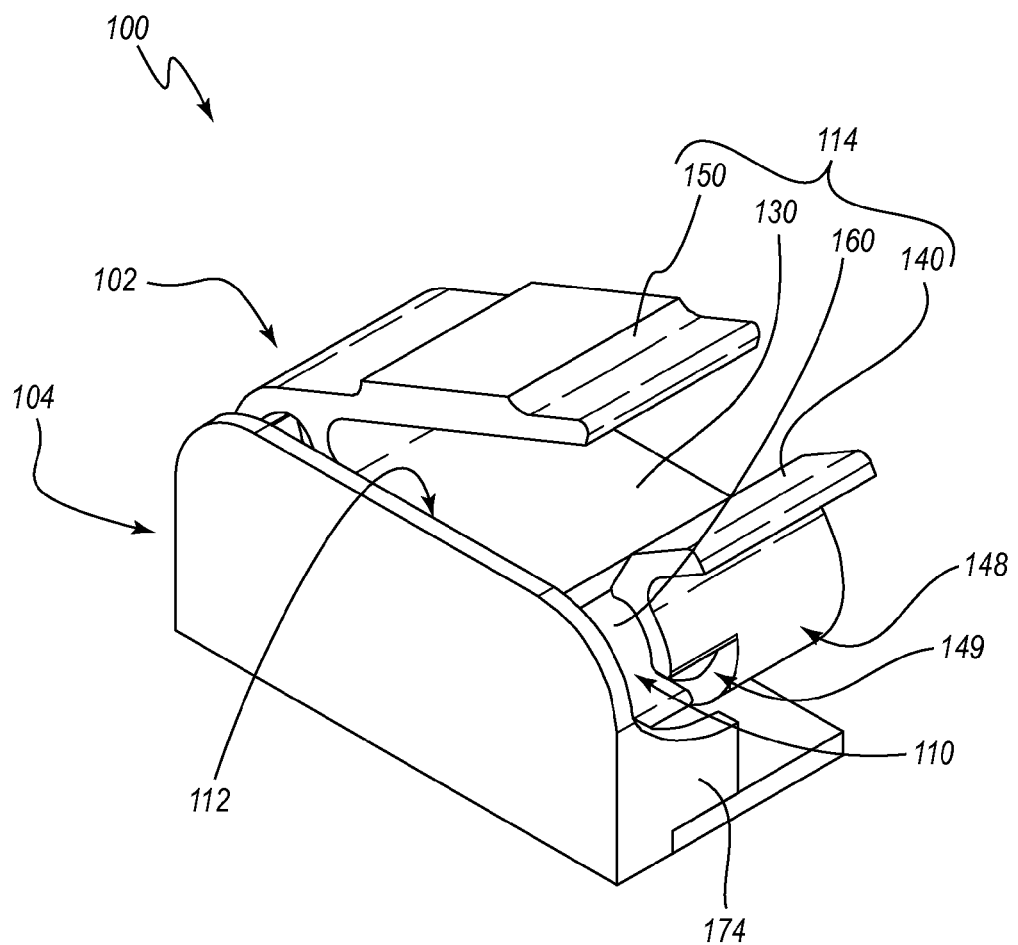
FIG. 1B is another perspective view of the holding device of FIG. 1A in the open state.

FIGS. 1A and 1B are separate perspective views directed toward generally opposite faces of an embodiment of a holding device 100. In certain embodiments, the holding device 100 can be configured to selectively receive and hold a catheter or any other suitable elongated instrument (see, e.g., FIGS. 2A-2E). The holding device 100 may also selectively release the elongated instrument. Further, in some arrangements, the holding device 100 can be configured to receive the elongated instrument therein while a proximal end of the elongated instrument is being gripped by a practitioner and while a distal end of the elongated instrument is at an interior of a patient. For example, in some instances, the holding device 100 may be particularly advantageous in certain procedures where a distal end of an elongated medical instrument has been inserted into a patient and oriented at a desired position with the patient. The holding device 100 may be fixed in place relative to an insertion site at which the elongated instrument enters the patient. In some arrangements, the fixed holding device 100 can prevent an elongated instrument that it holds from moving relative to the insertion site. For example, the holding device 100 can prevent the elongated instrument from being advanced further into the patient, from being retracted from the patient, and/or from rotating about a longitudinal axis of the elongated instrument.

In certain embodiments, the holding device 100 includes a retention portion, which may also be referred to as a retention member 102. The retention member 102 can generally correspond with the portion of the holding device 100 that is configured to retain at least a portion of an elongated instrument substantially stationary relative to the holding device 100. In further embodiments, the holding device 100 can include an insertion portion, which may also be referred to as an insertion member 104. The insertion member 104 can generally correspond with the portion of the holding device 100 that can aid in the introduction of an elongated device into the retention member. For example, as discussed below, in some instances the insertion member 104 can provide a desired insertion path along which an elongated instrument can be introduced into the retention member 102. In other or further embodiments, the insertion member 104 can include one or more features that assist in maintaining the elongated instrument within the retention member 102. Moreover, in some embodiments, an insertion path defined by the insertion member 104 may also serve as an exit path along which the elongated instrument may be removed from the holding device 100.

In the illustrated embodiment, the retention member 102 and the insertion member 104 are each formed by distinct pieces that are permanently joined together in any suitable manner. In other embodiments, a unitary piece of material may define at least a portion of each of the retention member 102 and the insertion member 104. For example, in some embodiments, the entire holding device 100 may be molded as a monolithic, unitary piece of material. In other embodiments, one or more of the retention member 102 and the insertion member can be molded and subsequently joined together.

In some embodiments, the insertion member 104 may be omitted. For example, the holding device 100 can be configured to selectively hold a portion of an elongated instrument and may be devoid of a region that can specifically assist in introducing the elongated instrument into the device, such as by passing the elongated instrument along a predefined insertion path.

In the illustrated embodiment, the holding device 100 includes a channel 110 (which may also be referred to as a holding channel or as a retention channel), an opening 112 (which may also be referred to as an insertion opening and/or as an exit opening), and a lock 114. An elongated instrument 200 (see FIG. 2A) can be introduced into the holding device 100 and/or removed from the holding device 100 via the opening 112. In the illustrated embodiment, the opening 112 is positioned between an upper end of the retention member 102 and the insertion member 104. Accordingly, in the illustrated embodiment, the retention member 102 and the insertion member 104 cooperate to define the opening 112. In other embodiments, the opening 112 may be defined solely by the retention member 102.

For example, in the illustrated embodiment, the insertion member 104 defines an insertion path 113 along which the elongated instrument 200 can be introduced into the channel 110, as discussed further below. That is, the elongated instrument 200 can be advanced through the opening 112 and along the insertion path 113 into the channel 110. In other embodiments, such as various embodiments in which the insertion member 104 is omitted, the opening 112 may lead directly into the channel 110. Stated otherwise the opening 112 may correspond directly with the channel 110 or be defined by the channel 110 itself.

The channel 110 can be configured to receive the elongated instrument 200 therein. In some embodiments, the channel 110 may be sized to receive elongated instruments that have a variety of different diameters or that have a variety of different maximum cross-sectional areas (e.g., where each cross-sectional area is taken along a plane that is perpendicular to a longitudinal axis of the elongated instrument).

The lock 114 can be configured to transition between an open state and a securing state, which may also be referred to as a closed state. The lock 114 can selectively retain the elongated instrument 200 in the channel 110 when in the securing state. In the illustrated embodiment, the lock 114 includes a retention arm 130, which may also be referred to as a spring, spring member, or retention member, and further includes a seat 160. The retention arm 130 and the seat 160 are configured to interact with each other to retain the elongated instrument 200 within the channel 110. In the illustrated embodiment, at least a portion of each of the retention arm 130 and the seat 160 define portions of the channel 110. Stated otherwise, at least a portion of the channel 110 may extend between the retention arm 130 and the seat 160. Other limits, contours, or boundaries of the illustrated channel 110 will be described further below.

As further discussed below, the lock 114 can further include a latch 140 that is configured to selectively interact with a locking arm 150, with may also be referred to as a locking member, to transition the lock 114 between the open and the securing states. In particular, the latch 140 may selectively retain an end of the locking arm 150, which can permit the retention arm 130 to press against the elongated instrument 200 within the channel 110. Releasing the latch 140 can permit the locking arm 150 and the retention arm 130 to return to a natural state in which the instrument 200 is no longer restrained by the holding device 100, as discussed further below.

The retention arm 130 can move toward the seat 160 as the lock 114 is transitioned from the open state to the securing state and can move away from the seat 160 as the lock 114 is transitioned from the securing state to the open state. In the illustrated embodiment, the retention arm 130 is connected to the locking arm 150. Movement of the locking arm 150 can effect movement of the retention arm 130. The retention arm 130 may be connected to the locking arm 150 at a hinge 136, which may also be referred to as an elbow, joint, transition region, or pivot.

With continued reference to FIGS. 1A and 1B, in some embodiments, the retention arm 130 comprises an elongated body 131 that extends between opposing ends 132, 134. The end 132 may be referred to as a distal end, and the end 134 may be referred to as a proximal end, with the distal and proximal terms being based on proximity to the hinge 136. In some embodiments, the body 131 comprises a flexible material. In further embodiments, the body 131 may be resiliently flexible so as to be able to repeatedly transition from a resting or natural state to a displaced or deformed state, and further, return to the natural state. In still further embodiments, the hinge 136 may be flexible. In the illustrated embodiment, the body 131 is substantially planar when in the natural state and is deflected to a bent orientation when in a displaced or deformed state. In the illustrated embodiment, the hinge 136 and the body 131 are integrally formed of a unitary monolithic piece of material.

In other embodiments, the body 131 of the retention arm 130 may be relatively stiff or inflexible. The retention arm 130 may be configured to flex only at the hinge 136. The distal end 132 of the spring may be able to grip the elongated instrument 200 as the retention arm 130 is urged toward the seat 160 and as potential energy is stored in the hinge 136 as the lock 114 is transitioned to the securing state. The hinge 136 may be resiliently flexible to return the body 131 of the spring to a natural or resting state when the lock 114 is returned to the open state.

The retention arm 130 may be moved via the locking arm 150. For example, in some instances, it may be said that the retention arm 130 is moved indirectly via the locking arm 150, as the locking arm 150 is directly contacted (e.g., via a finger of a practitioner) to effect movement of the retention arm 130. Stated otherwise, the locking arm 150 may be used to actuate the retention arm 130, or to cause the retention arm 130 to interact with the seat 160 or with an elongated instrument that is positioned between the retention arm 130 and the seat 160. The locking arm 150 may include a grip 154 for this purpose. In the illustrated embodiment, the grip 154 is a region of increased thickness 155, which can reinforce the locking arm 150. The grip 154 can include a region of increased friction 155 of any suitable variety, in some embodiments, such as a series of ridges and/or bumps, a different material having an increased coefficient of friction (e.g., an elastomeric material such as rubber), and/or any other suitable gripping feature. In some embodiments, the grip 154 may be used as a locating feature, which may provide visual and/or tactile information regarding a position at which the locking arm 150 can be touched to cause the arm to actuate to the securing state. The outer contours of the region of increased friction 155 is depicted as a substantially square region in FIG. 1A.

The locking arm 150 can be connected to the seat 160 via a hinge 152. In the illustrated embodiment, the hinge 152 defines a larger radius of curvature than does the hinge 136. In various embodiments, the hinge 152 may have a different flexibility than does the hinge 136. In other embodiments, the hinges 136, 152 have substantially the same flexibility.

In certain embodiments, the locking arm 150 may be configured to function as a resilient spring in manners that are the same or similar to the retention arm 130. For example, in the illustrated embodiment, the locking arm 150 can be relatively stiff or inflexible, and this substantial rigidity may be reinforced by the grip 154, which, as previously discussed, may include a region of increased thickness. The locking arm 150 may nevertheless pivot via the hinge 152, which can store potential energy as the lock 114 is transitioned from the open state to the closed state. The hinge 152 may be resiliently flexible to permit repeated transitions between the open and closed states.

When the latch 140 releases the distal end of the locking arm 150, the potential energy stored in the hinge 152 can automatically transition the locking arm 150 to its natural state. The potential energy stored in the hinge 136 may likewise assist in returning the locking arm 150 to its natural state, at least during a period in which the retention arm 130 interacts directly or indirectly (e.g., via an elongated instrument 200) with the seat 160.

In the illustrated embodiment, a notch 153 is provided in the hinge 152. The notch 153 defines a first end of the channel 110 through which the elongated instrument 200 can pass. The first end of the channel 110 can correspond with a first end 106 of the holding device 100. The device can further define a second end 108 that is opposite from the first end 106. The terms "first" and "second" do not necessarily denote a preferred orientation of the device 100. For example, in some instances, the first end 106 may be directed toward an insertion site at which the elongated instrument 200 enters the patient (see FIG. 10), whereas in other instances, the second end 108 may be directed toward the insertion site.

A distal end of the locking arm 150 (as determined based on proximity to the hinge 152) can include an angled face 156 that is configured to assist in transitioning the lock 114 to the securing state, as discussed further below. The distal end may include another angled face 158 that is configured to assist in maintaining the lock 114 in the securing state, as discussed further below.

With continued reference to FIGS. 1A and 1B, the latch 140 can include a grip 142, which may resemble the grip 154 discussed above. For example, the grip 142 may be manipulated in a direction away from the first end 106 of the holding device 100 to release the locking arm 150 and thus transition the lock 114 from the securing orientation to the open orientation. In the illustrated embodiment, the grip 142 is positioned on a protrusion that extends generally upwardly at the second end 108 of the holding device 100. The latch can include a hinge 148 that may be resiliently flexible.

The latch 140 can include an angled face 144 that is configured to interact with the angled face 156 of the locking arm 150 as the holding device 100 is transitioned from the open state to the closed state. In particular, the faces 144, 156 may be configured to slide past one another in a manner that causes the latch 140 to be urged outwardly toward the second end 108 of the holding device 100 as the locking arm 150 is pressed downwardly toward the seat 160.

The latch 140 can further include a retaining face 146 that is configured to interact with the face 158 of the arm to maintain the holding device 100 in the closed state. In particular, after the locking arm 150 has been compressed downwardly toward the seat 160 by a sufficient amount, the latch 140 can spring back to a natural position. In this position, the face 146 may be above the face 158. When the compressive force is no longer applied to the locking arm 150, the locking arm 150 may be permitted to begin a resilient return to its natural state. However, the retaining face 146 can engage the face 158 of the locking arm 150 to prevent the arm from fully returning to its natural position, thus maintaining the holding device 100 in the closed state.

Locks 114 other than that described above with respect to the latch 140 and the locking arm 150 are also possible. For example, the locking arm 150 and the retention arm 130 may be retained in a compressed state via a separate clamp (not shown), such as a ratcheting vice grip, that provides compressive forces to a bottom of the seat 160 and a top of the locking arm 150 at the second end 108 of the holding device 100. Any other suitable locking arrangement is also contemplated. The illustrated embodiment of the lock 114 can be advantageous in some instances, as the lock 114 may be manipulated into the securing state and/or may be manipulated into the open state by a practitioner with the use of a single hand.

In some embodiments, the lock 114 may be moved to each of the securing state and the open state by urging separate components thereof generally in the same direction. For example, as shown in FIGS. 2C and 2D, and discussed further below, generally downward forces may be applied separately to the locking arm 150 and the latch 140 to separately transition the lock 114 to the securing state and the open state, respectively. Such an arrangement can be advantageous, in some instances, as the device 100 can rest or be mounted upon a single surface, which can provide a reactive force to counter the forces applied to the various components of the lock 114 during locking or opening of the device. Thus, in some instances, the device 100 may be manipulated via a single finger. In other instances, the device 100 may be held within a practitioner's hand, such as within a closed fist, and the curled fingers of a hand may provide the reactive surface while the thumb may be used to manipulate either the locking arm 150 or the latch 140 to effect closing or opening of the lock 114, respectively.

In the illustrated embodiment, a notch 149 is provided in the hinge 146. The notch 149 defines a second end of the channel 110 through which the elongated instrument can pass. The second end of the channel 110 can correspond with the second end 108 of the holding device 100.

In the illustrated embodiment, the seat 160 extends longitudinally between the hinges 146, 152. The seat 160 can be arranged as a platform against which the elongated instrument 200 can rest. In some embodiments, the seat 160 defines a substantially planar surface. A base 161 of the holding device 100 can include the seat 160. In the illustrated embodiment, the base 161 further includes a support 162 that extends outwardly from a neck 164 toward each of the first and second ends 106, 108 of the holding device 100. In the illustrated embodiment, the neck 164 is oriented between the seat 160 and the support 162. Portions of the seat 160 that are not constrained by the support 162 can contribute to the flexibility of the hinges 148 and 152 to allow the hinges to deflect elastically as the holding device 100 is changed between the holding state and the open state. The support 162 can stabilize the holding device 100 during use thereof. In some instances, material costs may be reduced by providing spaces between the seat 160 and the support 162. The neck 164 can permit such spacing. In some embodiments, the neck 164 can define a coupling channel 166 via which the retaining member 102 can be joined to the insertion member 104, as discussed further below with respect to FIGS. 11A and 11B.

Further discussion of operation of the retaining member 102 is provided below with respect to FIGS. 2A-8. Various features of the insertion member 104 will now be described with respect to FIGS. 1A and 1B, and also will be described below with respect to FIGS. 2A-3C.

The insertion member 104 can include a sidewall 170. In the illustrated embodiment, the sidewall 170 is oriented at approximately a 90 degree angle relative to the seat 160. In various embodiments, the sidewall 170 and the seat 160 can be oriented at an angle relative to each other that is within a range of from about 45 degrees to about 135 degrees, from about 60 degrees to about 120 degrees, or from about 85 degrees to about 95 degrees. Further, in the illustrated embodiment, the sidewall 170 and the seat 160 include substantially planar portions that are oriented at an angle relative to each other. For example, in various embodiments, the planar portions of the sidewall 170 and the seat 160 can be oriented at an angle relative to each other that is within a range of from about 45 degrees to about 135 degrees, from about 60 degrees to about 120 degrees, or from about 85 degrees to about 95 degrees. Other arrangements are also possible.

In the illustrated embodiment, a ramp 172 extends inwardly from the sidewall 170 toward the channel 110. The ramp 172 can assist in directing the elongated member 200 into the channel 110. In the illustrated embodiment, the sidewall 170 and the ramp 172 each define portions of the insertion path 113 discussed above.

At each of the first and the second ends 106, 108 of the holding device 100, the insertion member 100 can include protrusions 173, 174, respectively, that project inwardly from the sidewall 170. The protrusions 173, 174 may serve to stabilize the sidewall 170 relative to the support 162. In some embodiments, the protrusions 173, 174 define end portions of the ramp 172. The protrusions 173, 174 may assist in guiding the elongated instrument 200 into the channel 110. In some embodiments, a portion of each of the protrusions 173, 174 may define portions of opposing ends of the channel 110, as depicted, for example, in FIGS. 3A-3C.

In some embodiments, the insertion member 104 includes a retaining ridge 176 that is configured to maintain the elongated instrument 200 within the channel 110. This feature is discussed further below with respect to FIG. 3C.

With continued reference to FIGS. 1A and 1B, and with further reference to FIGS. 3A-4B, in the illustrated embodiment, the channel 110 can extend longitudinally from the first end 106 to the second end 108 of the holding device 100. The channel 110 can extend laterally between the outer edges of the retention arm 130 and the seat 160. Likewise, the upper and lower ends of the channel 110 may be defined, at least in part, by the lower surface of the retention arm 130 and by the upper surface of the seat 160. As the retention arm 130 is movable toward and away from the seat 160, at least a portion of the channel 110 may be variable in size.

Figure 2A:
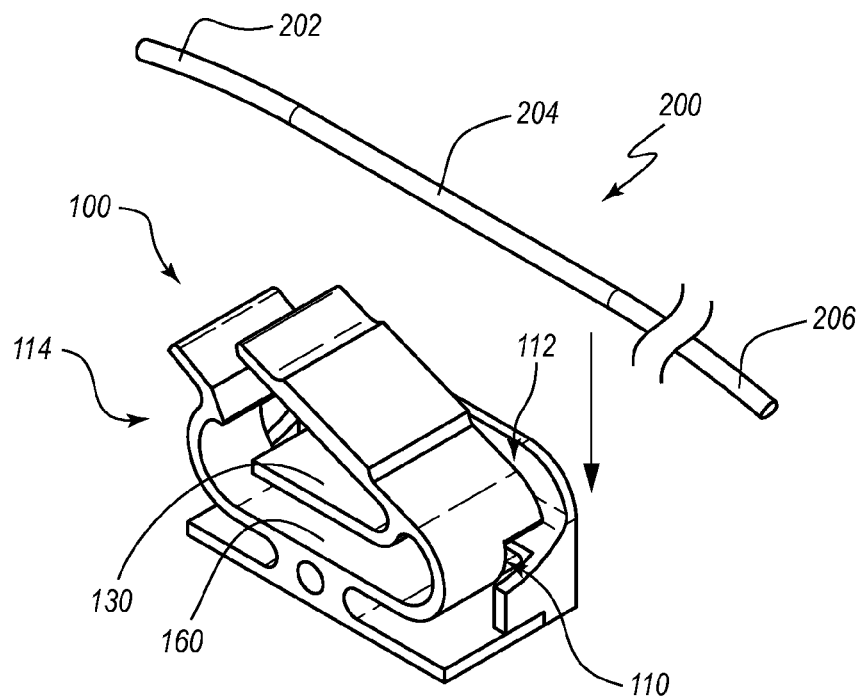
FIG. 2A is a perspective view of the holding device of FIG. 1A in an early stage of being coupled to an embodiment of an elongated instrument—in particular, a catheter—wherein the holding device is in the open state.
Figure 2B:
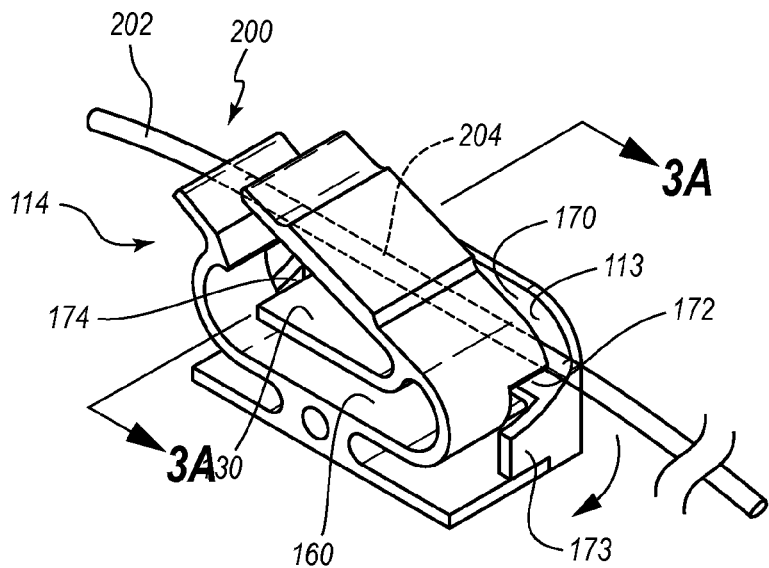
FIG. 2B is another perspective view of the holding device of FIG. 1A at a later stage of being coupled to the catheter, wherein movement of the catheter along a ramp portion of the device is depicted while the holding device is in the open state.
Figure 2C:
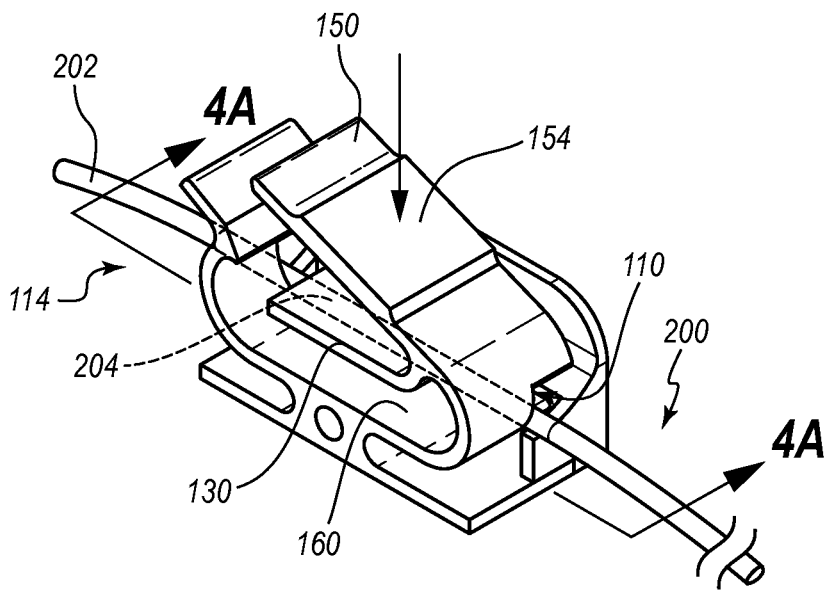
FIG. 2C is another perspective view of the holding device of FIG. 1A at a later stage of being coupled to the catheter, wherein the catheter has been introduced into a channel portion of the holding device while the device is in the open state.
Figure 2D:
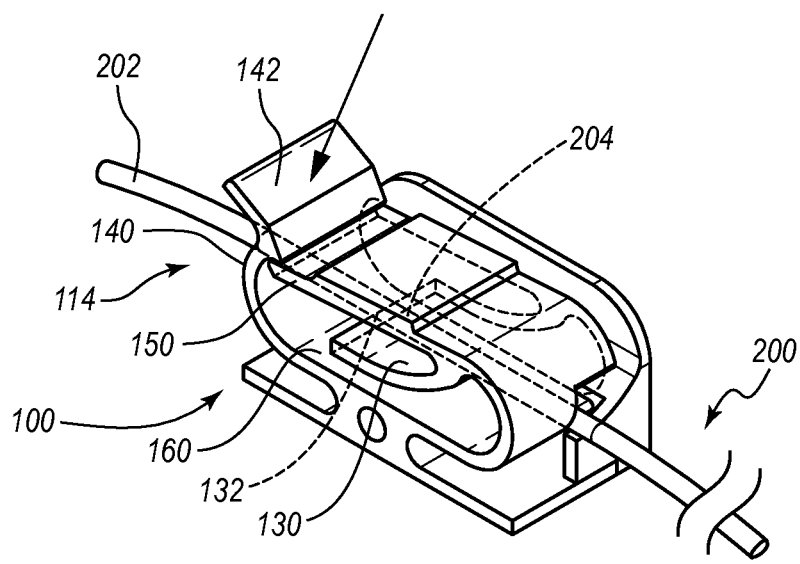
FIG. 2D is another perspective view of the holding device of FIG. 1A at a later stage of being coupled to the catheter, wherein the holding device is depicted as having been transitioned to a securing state to retain the catheter within the channel portion.

FIGS. 2A-2E depict various stages of an illustrative method of using the holding device 100. FIG. 2A is a perspective view of the holding device 100 in an early stage of being coupled to an embodiment of an elongated instrument 200. In the illustrated embodiment, the elongated instrument 200 is a catheter that includes a proximal end 202, an intermediate portion 204, and a distal end 206. The distal end 206 may be positioned at any desired location, such as within a patient, and in some embodiments, the proximal end 202 may be used in the placement procedure. In other embodiments, the distal end 206 of the elongated instrument 200 may be positioned at an exterior of a patient and/or in any other desired orientation. In the stage illustrated in FIG. 2A, the lock 114 is shown in the open state.

An arrow depicts that the intermediate portion 204 of the catheter 200 can be inserted into the opening 112.

FIG. 2B depicts a later stage of the illustrative method of using the holding device 100. At this stage, the intermediate portion 204 of the catheter 200 is being moved along the insertion path 113. In particular, the intermediate portion 204 is shown being urged inwardly toward the channel 100 via the ramp 172. In subsequent stages, opposite ends of the intermediate portion 204 of the catheter will continue to be urged inwardly via the protrusions 173, 174. These opposite ends of the intermediate portion 204 may rest on the protrusions 173, 174 when a region of the intermediate portion 204 that is positioned between the opposite ends is oriented between the retention arm 130 and the seat 160, as depicted in FIG. 2C.

Figure 3A:
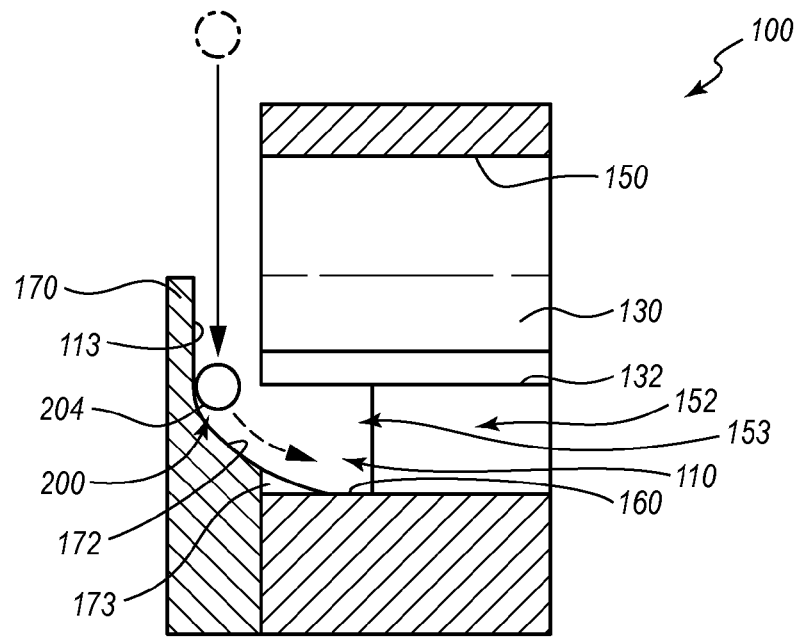
FIG. 3A is a cross-sectional view of the holding device of FIG. 1A taken along the view line 3A-3A in FIG. 2B, wherein an insertion path along which the catheter is advanced for introduction into the channel is shown.

In the illustrated embodiment, the insertion path 113 is curved. For example, the insertion path 113 smoothly transitions from the sidewall 170 toward the seat 160 via the ramp 172. The illustrated insertion path 113 is substantially orthogonal to a longitudinal axis of the intermediate portion 204 of the elongated instrument 200, as shown in FIG. 2B. This substantially orthogonal orientation may be maintained throughout insertion of the elongated instrument 200 into the channel 110. For example, as can be seen in FIG. 3A, a longitudinal axis of the intermediate portion 204 (extending into and out of the page) is substantially orthogonal to a plane that contains the arrow that depicts the movement of the elongated instrument 200. As used herein, the term "substantially orthogonal" includes an exactly orthogonal orientation and/or an orientation that is generally orthogonal (i.e., from about 80 degrees to about 100 degrees).

FIG. 2C depicts a stage at which the intermediate portion 204 of the catheter 200 is positioned within the channel 110. The lock 114 is depicted in the open state, but the downwardly directed arrow indicates that application of force to the grip 154 can move the locking arm 150 downwardly for purposes of securing the lock 114. As the locking arm 150 is moved down, the retention arm 130 and the seat 160 will engage the intermediate portion 204 of the catheter 200. It may be said that the lock 114 may be selectively transitioned from the open state to the securing state by a practitioner, as the practitioner can selectively move the locking arm 150 in the manners described to effect such a transition.

With the lock 114 in the open state and the catheter 200 within the channel 110, the catheter 200 can be freely movable within the channel 110 relative to the holding device 100. For example, the catheter 200 may be moved longitudinally in the distal and/or the proximal direction. The catheter 200 may further be rotated about a longitudinal axis of the catheter 200.

FIG. 2D depicts the holding device 100 in the securing state. In this orientation, the latch 140 engages the locking arm 150 in the manner described above. The distal end 132 of the retention arm 130 presses the intermediate portion 204 of the catheter 200 against the seat 160. In some embodiments, the retention arm 130 and the seat 160 can compress the catheter 200. Stated otherwise, in some embodiments, the catheter 200 may comprise a compressible material, and the retention arm 130 and/or the seat 160 may deform (e.g., elastically deform) the catheter 200. In some embodiments, an edge of the distal end 132 of the spring 132 may dig into flexible material of catheter 200 to create a transversely oriented ridge that prevents longitudinal movement of the catheter 200. Such a ridge formation may also prevent rotation of the catheter 200 about a longitudinal axis thereof. The retention arm 130 and the seat 160 may similarly prevent longitudinal movement and/or rotational movement of the catheter 200 when such a ridge is not formed and/or when an elongated instrument that is held or gripped thereby is not compressible. In general, when the lock 114 is in the securing state, it can retain the catheter 200 within the channel 110 in any suitable manner.

The lock 114, and in particular the retention arm 130 and the seat 160, can prevent movement of the intermediate portion 204 of the catheter 200 relative to the holding device 100. In some instances, the intermediate portion 204 of the catheter 200 is prevented from moving longitudinally (e.g., in the distal and/or proximal directions) within the channel 110. In other or further instances, the intermediate portion 204 of the catheter 200 is prevented from rotating about a longitudinal axis of the catheter 200. Such prevention of rotational movement of the intermediate portion 204 relative to the holding device 100 may be referred to as torque locking. For example, in some procedures, after placement of the catheter 200 within a patient, a residual amount of torque may be present in the catheter 200. It may be desirable to maintain this residual torque on the catheter 200 to ensure that the catheter 200 remains in a desired position relative to the patient. When the lock 114 is moved to the securing state, the torque locking provided thereby can maintain the desired residual torque on the catheter 200. The catheter 200 may thus be released (e.g., by a practitioner) after the lock 114 has been actuated in this manner. In some instances, the holding device 100 may thus free a practitioner to use a hand that would otherwise be used to maintain the catheter 200 at a desired longitudinal position and/or to maintain the desired residual torque on the catheter 200.

In some embodiments, the retention arm 130 and/or the seat 160 can include one or more gripping surfaces to increase frictional engagement with an elongated instrument. In various embodiments, the one or more gripping surfaces can include one or more of ridges; grooves; coatings; high-frictional material inserts, attachments, overmoldings, etc. (e.g., rubber); and/or any other suitable feature.

With continued reference to FIG. 2D, an arrow depicts a direction in which the grip 142 portion of the latch 140 can be manipulated or displaced to transition the lock 114 from the securing state to the open state. It may be said that the lock 114 may be selectively transitioned from the securing state to the open state by a practitioner, as the practitioner can selectively move the latch 140 in the manners described to effect such a transition.

Figure 2E:
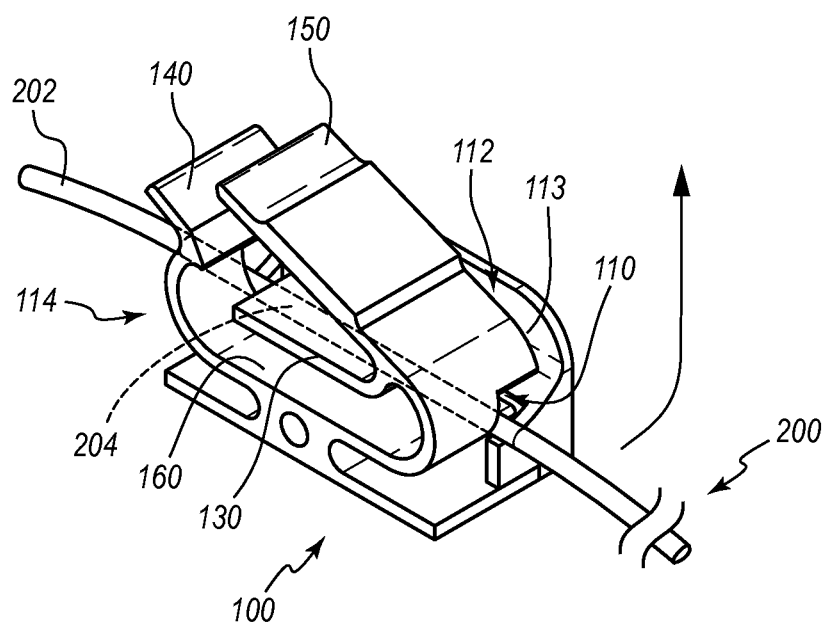
FIG. 2E is another perspective view of the holding device of FIG. 1A that depicts a stage of a decoupling procedure, wherein the device is depicted as having been transitioned to an open state again and an arrow depicts a path that the catheter may be moved along for removal from the device.

FIG. 2E depicts the holding device 100 after the lock 114 has been returned to the open state. In particular, release of the locking arm 150 from the latch 140 can permit the locking arm 150 and the retention arm 130 to return to their natural states. The retention arm 130 can be separated from the seat 160, thus opening the channel 110. An arrow depicts a path that the intermediate portion 204 of the catheter 200 can follow in exiting the holding device 100. In particular, the catheter 200 can move along the insertion path 113 and through the opening 112, in the reverse direction from that depicted in FIGS. 2A-2C, as it is decoupled from the holding device 100.

FIG. 3A is a cross-sectional view of the holding device 100 taken along the view line 3A-3A in FIG. 2B. The insertion path 113 is shown in greater detail, and a course traveled by the catheter 200 in traveling along the insertion path 113 is depicted via arrows. Various features of the holding device 100 that have previously been discussed are again identified to provide a further understanding of their relative arrangements in the illustrated embodiment. For example, the locking arm 150, the retention arm 130 and the end 132 thereof, and the seat 160 are identified.

Figure 3B:
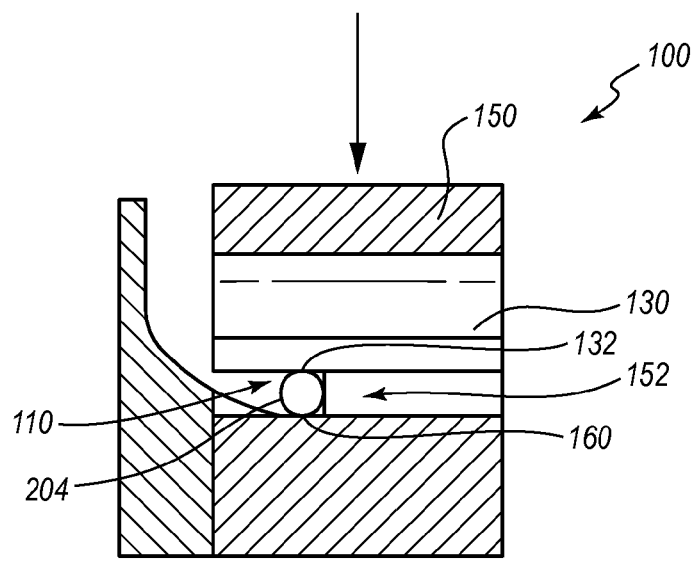
FIG. 3B is another cross-sectional view of the holding device of FIG. 1A, such as that depicted in FIG. 3A, wherein the device is depicted being transferred to a closed state for retaining the catheter within the channel.

FIG. 3B depicts the retention arm 130 being compressed as the locking arm 150 is moved downwardly toward the seat 160 to transition the lock 114 to the closed state. Compression of the retention arm 130 can give rise to a holding force that retains the intermediate portion 204 of the catheter 200 within the channel 110. In the arrangement shown in FIG. 3B, in inner wall of the hinge 152, which defines the notch 153 (see also FIG. 3A) acts as a stop that prevents the catheter 200 from moving out of the channel 110 in a rightward direction in the orientation depicted in FIG. 3B. In like manner, an inner wall of the hinge 148, which defines the notch 149 can act as a stop that prevents the catheter 200 from moving out of the channel 110 (compare FIGS. 1B and 2C with FIG. 3B). As previously mentioned, in some embodiments, the retention arm 130 can include a friction-enhancing feature to aid in maintaining the catheter 200 at a desired position within the channel 110. For example, the retention arm 130 can include one or more ridges or grooves.

Figure 3C:
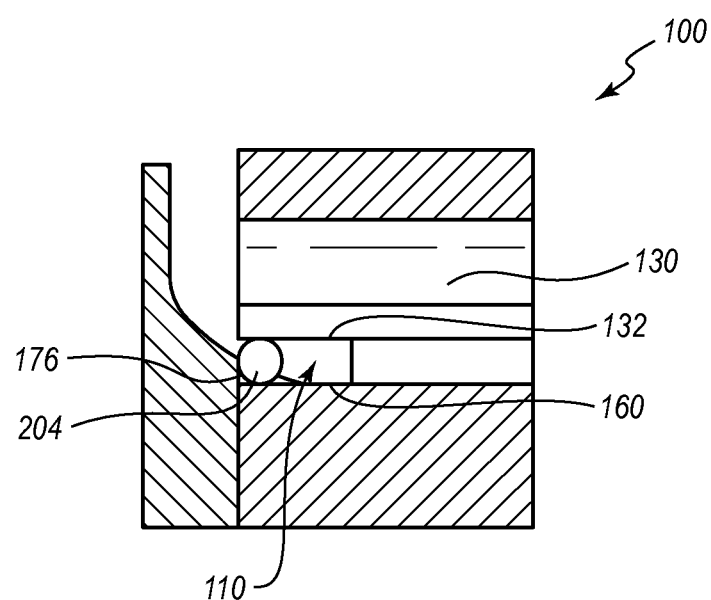
FIG. 3C is another cross-sectional view of the holding device of FIG. 1A, such as that depicted in FIG. 3A, wherein the device is depicted in the closed state with the catheter in contact with a retaining ridge that assists in maintaining the catheter within the channel while the device is in the closed state.

FIG. 3C illustrates that the retaining ridge 176 can assist in maintaining the intermediate portion 204 of the catheter 200 within the channel 100 when the lock 114 is in the closed state. In particular, with the retention arm 130 in close proximity to the seat 160, the retaining ridge 176 may prevent the intermediate portion 204 from exiting the channel 110 in a direction opposite of that discussed above (i.e., leftward in the depicted orientation).

Figure 4A:
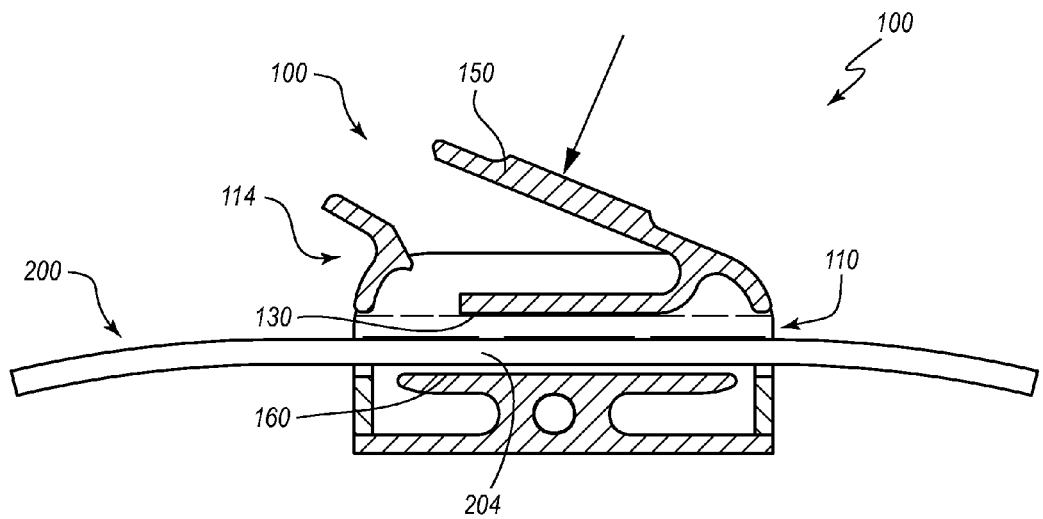
FIG. 4A is a cross-sectional view of the holding device of FIG. 1A taken along the view line 4A-4A in FIG. 2C, wherein the channel is shown in greater detail with the device in the open state.

FIG. 4A is a cross-sectional view of the holding device 100 taken along the view line 4A-4A in FIG. 2C. The holding device 100 is shown in the open state with the retention arm 130 distanced from the seat 160.

Figure 4B:
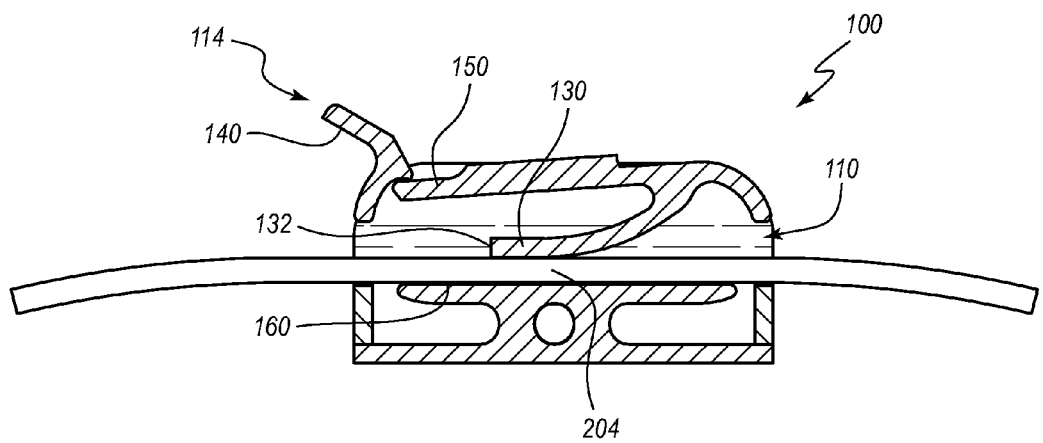
FIG. 4B is another cross-sectional view of the holding device of FIG. 1A, such as that depicted in FIG. 4A, wherein the device is depicted as having been transferred to the closed state for retaining the catheter within the channel.

FIG. 4B is another cross-sectional view of the holding device 100 shown in the closed state. The retention arm 130 is shown having been elastically deformed. The retention arm 130 provides a holding force that is capable of retaining the catheter 200 within the channel 110, as discussed above. For example, in various embodiments, the holding force and holding orientation provided by the spring can prevent the intermediate portion 204 of the catheter 200 from moving longitudinally (e.g., left or right in the illustrated orientation) relative to the holding device 100 and/or can prevent the intermediate portion 204 of the catheter 200 from rotating about a longitudinal axis of the catheter 200, as determined relative to the holding device 100.

Figure 5:
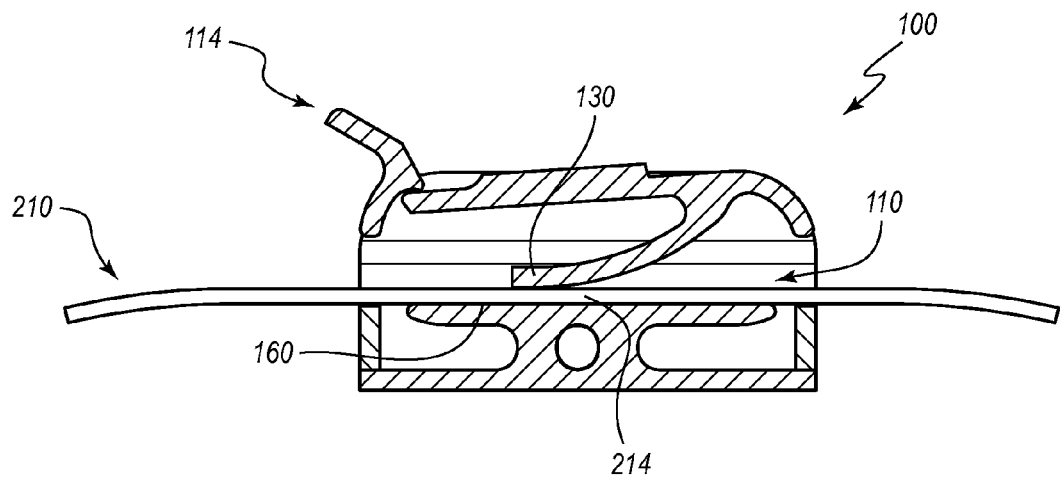
FIG. 5 is another cross-sectional view of the holding device of FIG. 1A, such as that depicted in FIG. 4B, wherein an elongated instrument having a smaller diameter than that of the catheter of FIG. 4B is shown being retained in the channel.

FIG. 5 is another cross-sectional view of the holding device 100 in which an elongated instrument 210 having a smaller diameter than that of the catheter 200 is shown being retained in the channel 110. Although the retention arm 130 is deformed by a lesser amount than it is in FIG. 4B, the retention arm 130 nevertheless provides sufficient retentive force to prevent movement of an intermediate portion 214 of the elongated instrument 210 relative to the holding device 100. The elongated instrument 210 may be of any suitable variety, such as, for example, a catheter.

In various embodiments, the channel 110 can be configured to receive therein an elongated instrument 200 that has a diameter within a range of acceptable different values. Moreover, the holding device 100 can be configured to retain the elongated instrument within the channel 110, in manners such as described, above for any of the diameters. For example, in some embodiments, the channel 110 may be sized to receive and/or operate with a catheter of typical size, such as a catheter having a gauge of from 3 French to 34 French, or any subset thereof. In some embodiments, the holding device 100 may be operable with elongated instruments having diameters within a range of from about 0.5 millimeters to about 12 millimeters (e.g., a range that encompasses typical catheter sizes), or any subset thereof. In various embodiments, the holding device 100 may be operable with elongated instruments having diameters that are within a range of from about 1 millimeter to about 20 millimeters, from about 1 millimeter to about 10 millimeters, or from about 1 millimeter to about 5 millimeters. In other embodiments, the holding device 100 can be operable with elongated instruments having diameters that are no greater than about 5, about 10, about 15, about 20, or about 25 millimeters. Other ranges are also possible, depending on application or use of the holding device 100.

Figure 6:
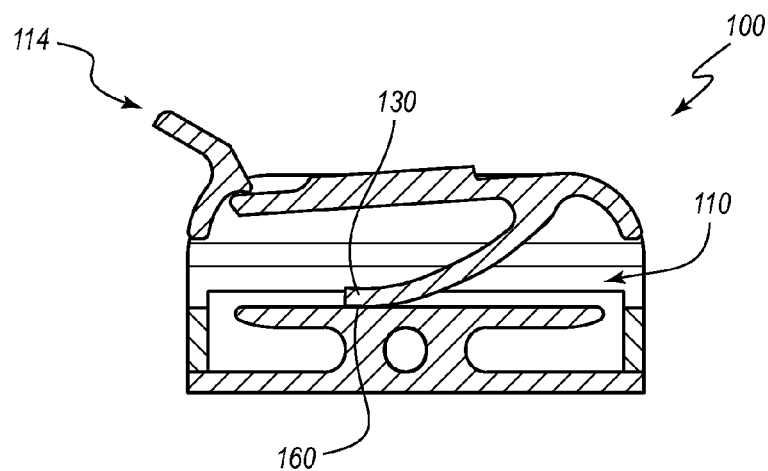
FIG. 6 is another cross-sectional view of the holding device of FIG. 1A, such as that depicted in FIG. 4B, wherein the device is shown in a closed state without any elongated instruments within the channel.

FIG. 6 is another cross-sectional view of the holding device 100 in which the channel 110 is empty, or stated otherwise, in which no elongated instruments are retained in the channel 110. Although the retention arm 130 is deformed by a lesser amount than it is in FIG. 5, the retention arm 130 nevertheless provides a force relative to the seat 160. It may be stated that the seat 160 provides a preload to the retention arm 130. Accordingly, regardless of the diameter size of an elongated instrument that is positioned within the channel 110, the retention arm 130 can load the elongated instrument. In some embodiments, the preload provided to the retention arm 130 by the seat 160 would be sufficient to prevent movement of an elongated instrument relative to the holding device 100, if the same preload force were applied by the retention arm 130 to the elongated instrument. However, in various embodiments, the force provided by the retention arm 130 to any elongated instrument that is introduced into the channel 100 exceeds the preload force, as the presence of the elongated instrument may lead to an additional elastic deformation of the retention arm 130.

Figure 7:
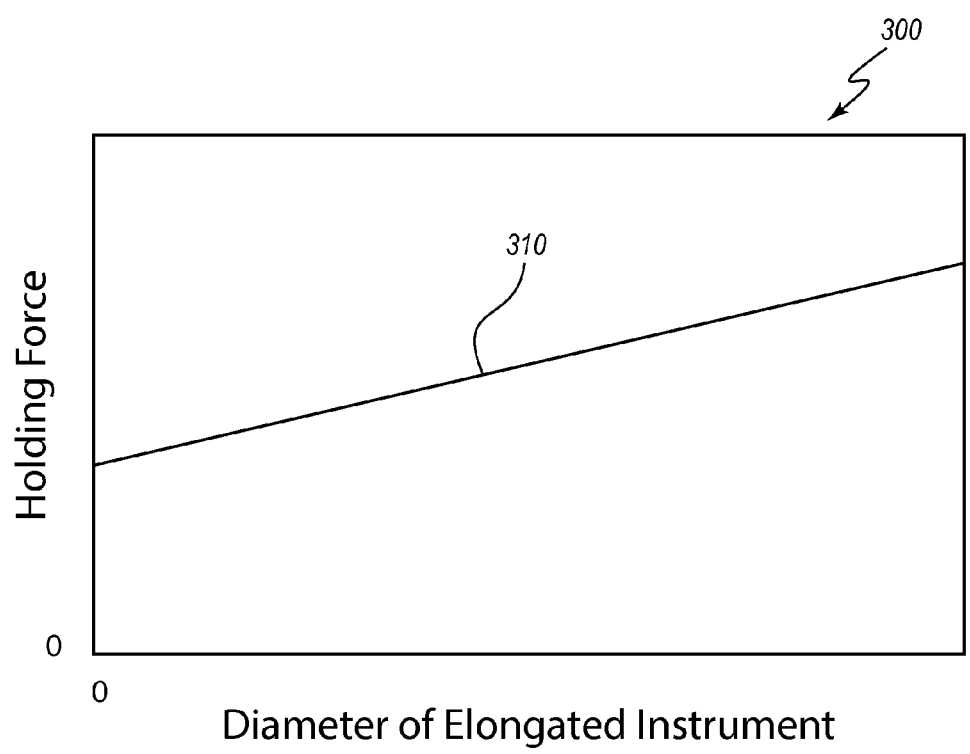
FIG. 7 is a plot that depicts the holding force provided by the device of FIG. 1A as a function of the diameter of an elongated instrument that is retained within the channel of the device, wherein a non-zero holding force is provided in the absence of an elongated instrument (i.e., the force provided at a zero-value diameter)

This concept is depicted in FIG. 7, which is a plot 300 of the holding or retentive force provided by an embodiment of the holding device 100 as a function of the diameter of an elongated instrument that is retained within the channel of the device. As can be seen from the curve 310, a non-zero holding force is provided in the absence of an elongated instrument. This value, where the diameter is 0, is the preload force that is present when the retention arm 130 directly contacts the seat 160.

Figure 8A:
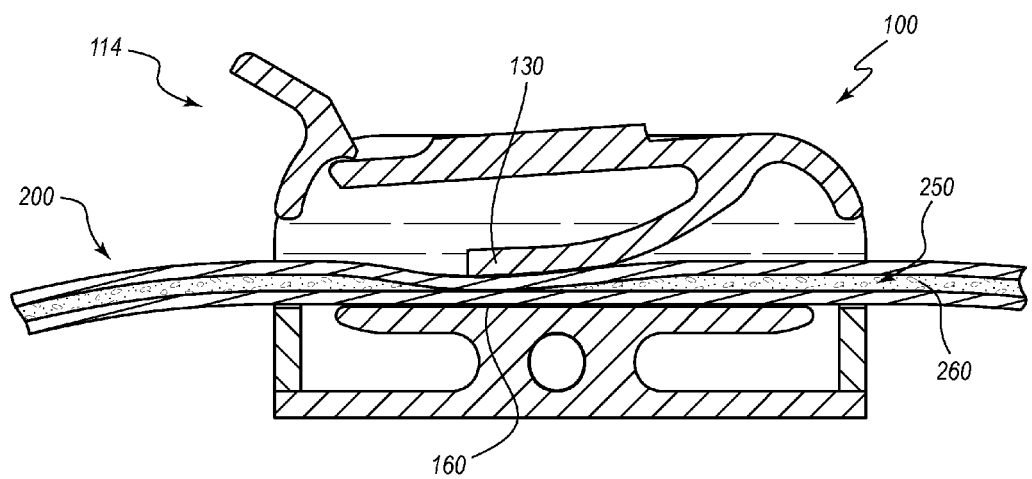
FIG. 8A is another cross-sectional view of the holding device of FIG. 1A that is slightly offset relative to that depicted in FIG. 4B such that the cross-section extends through the catheter, wherein the device is shown operating as a pinch valve and providing sufficient pinching force to prevent fluid flow.

With reference to FIG. 8A, in some embodiments, the retention arm 130 and the seat 160 can cooperate to close a lumen 250 of the elongated instrument 200. The lumen 250 can be configured to carry a flow of fluid 260, in some instances, and the retention arm 130 and the seat 160 can cooperate to stop the fluid flow. In particular, the retention arm 130 and the seat 160 can provide a sufficient pinching force to prevent or stop fluid flow. The holding device 100 thus may operate as a pinch valve. In some embodiments, the holding device 100 is operable as a pinch valve for any of multiple tubes and/or catheters that have a variety of different diameters one from another.

Figure 8B:
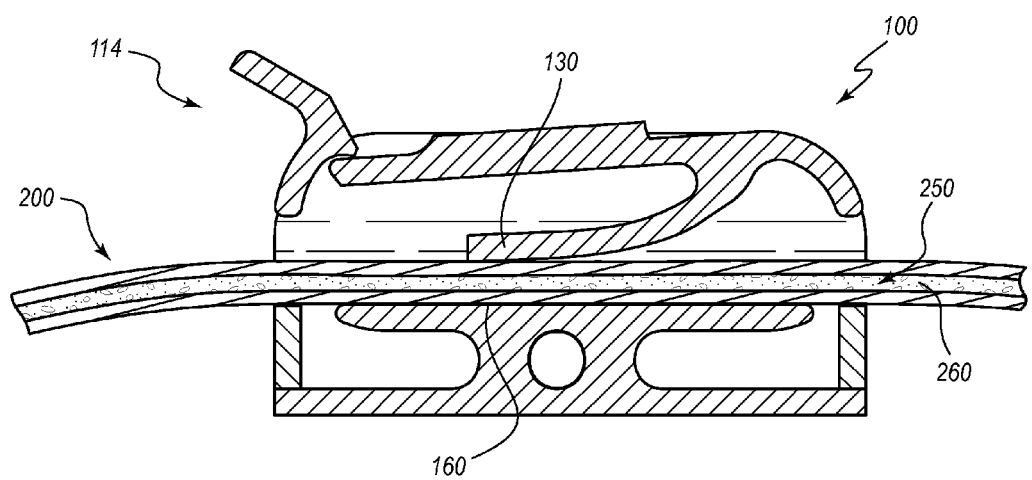
FIG. 8B is a cross-sectional view of the holding device of FIG. 1A such as the view provided in FIG. 8A, wherein the device is shown operating as a check valve, where fluid within the catheter is at a pressure that is sufficiently high to overcome a closing force provided by the holding device.

With reference to FIG. 8B, in some embodiments, the holding device 100 is operable as a check valve for the flow of fluid 260 through the elongated instrument 200. For example, in some embodiments, the pinching force provided by the retention arm 130 in cooperation with the seat 160 may be configured to permit fluid flow when the pressure of the fluid 260 within the lumen 250 is at or above a threshold value, and may be configured to close the lumen 250 when the fluid pressure is below the threshold value. In some embodiments, the retention arm 130 and the seat 160 can provide sufficient pinching force to prevent the elongated instrument 200 from moving relative to the holding device 100 independent of the fluid pressure with the lumen 250 (e.g., regardless of whether the fluid pressure is above or below the threshold value). For example, in some embodiments, the retention arm 130 and the seat 160 can cooperate to close the lumen 250. Fluid pressure may rise within the lumen to a point where the retention arm 130 is moved away from the seat 160 sufficiently to permit fluid flow through the lumen 250, or stated otherwise, the pressure can become sufficient to overcome the preload of the spring. The pressure of the fluid 260 may again drop below the threshold value, at which point the spring force may overcome the fluid pressure within the elongated instrument 200 such that the retention arm 130 and the seat 160 again close the lumen 250.

As previously mentioned, and as mentioned elsewhere herein, the holding device 100 may be used in contexts other than medical contexts. Accordingly, in some instances, the holding device 100 may be used as a pinch valve and/or as a check valve in contexts other than a healthcare setting. For example, the holding device 100 may be used with any suitable tube and/or with any suitable fluid, whether the fluid is in a liquid or gaseous state (or a combination thereof).

Figure 9:
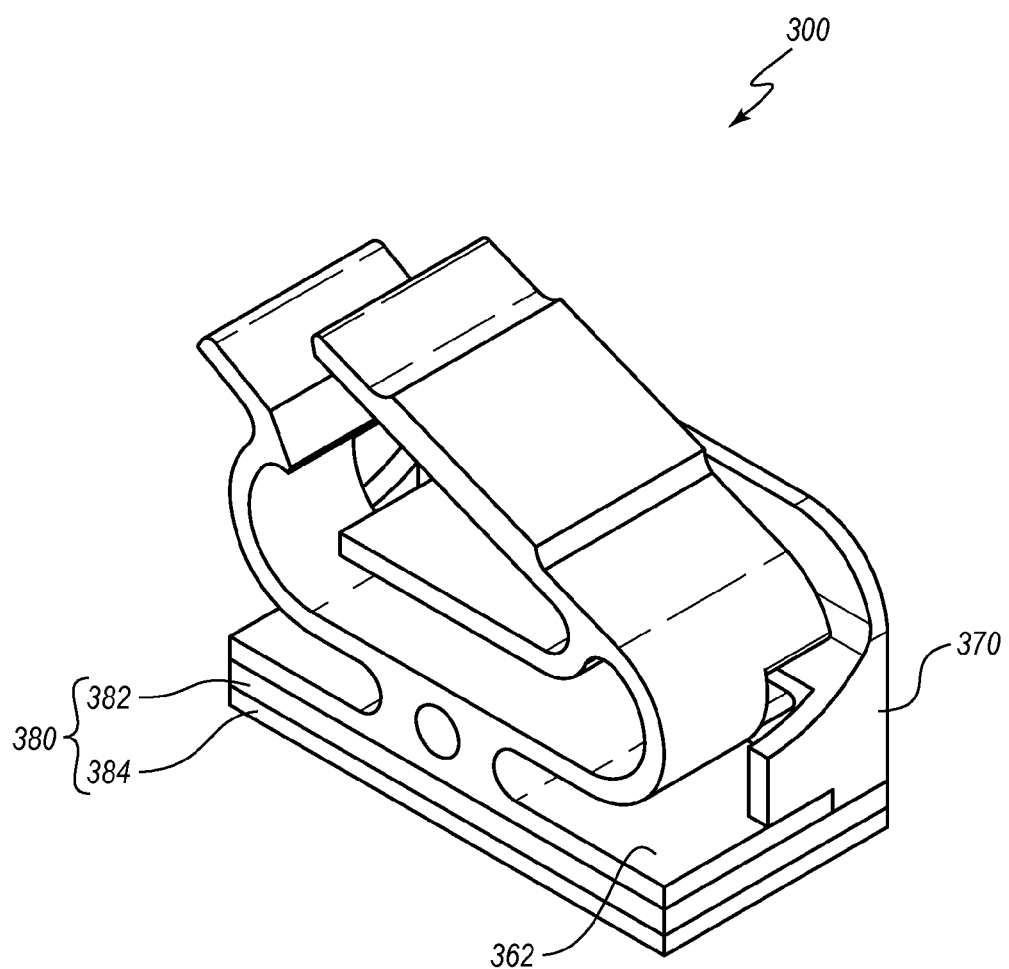
FIG. 9 is a perspective view of another embodiment of a holding device that includes a fastener for attaching the device to a separate object.

FIG. 9 is a perspective view of another embodiment of a holding device 300 that resembles the holding device 100 in many respects. Accordingly, like features are designated with like reference numerals, with the leading digits incremented to "3." Relevant disclosure set forth above regarding similarly identified features thus may not be repeated hereafter. Moreover, specific features of the device 300 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the device 300. Any suitable combination of the features and variations of the same described with respect to the device 100 can be employed with the device 300, and vice versa. This pattern of disclosure applies equally to further embodiments depicted in subsequent figures and described hereafter, wherein the leading digits may be further incremented.

The holding device 300 can include a fastener 380 that is configured to attach the holding device 300 to a separate object. For example, the fastener 380 may be configured to fixedly secure the holding device 300 to a patient (e.g., to the skin of the patient) or to an object that is fixed relative to the patient, such as when the patient is immobile (e.g., anesthetized). The fastener 380 may be attached to any suitable object, such as an object having a sufficient mass and immobility (or fixation) to allow the holding device 300 to control a position of the elongated instrument 200 when the holding device 300 is fixedly secured to the object and is in the holding state.

The illustrated fastener 380 includes an adhesive layer 382 and a removable non-sticking layer or backing 384. The adhesive layer 382 is fixedly secured to a bottom surface of a support 362 and a sidewall 370 of the illustrated device 300. More generally, the adhesive layer 382 may be said to be joined to a base portion of the device 300. In some embodiments, the adhesive layer 382 is fixedly secured to the device 300, yet is configured to provide a secure but temporary attachment to the object to which the device 300 is attached. For example, the adhesive layer 382 may comprise any suitable temporary adhesive. The fastener 380 can comprise any other suitable arrangement. For example, in some embodiments, the fastener 380 may comprise one or more of a strap, a belt, a buckle, a clip, a zip tie, or any other suitable fastening device.

Figure 10:
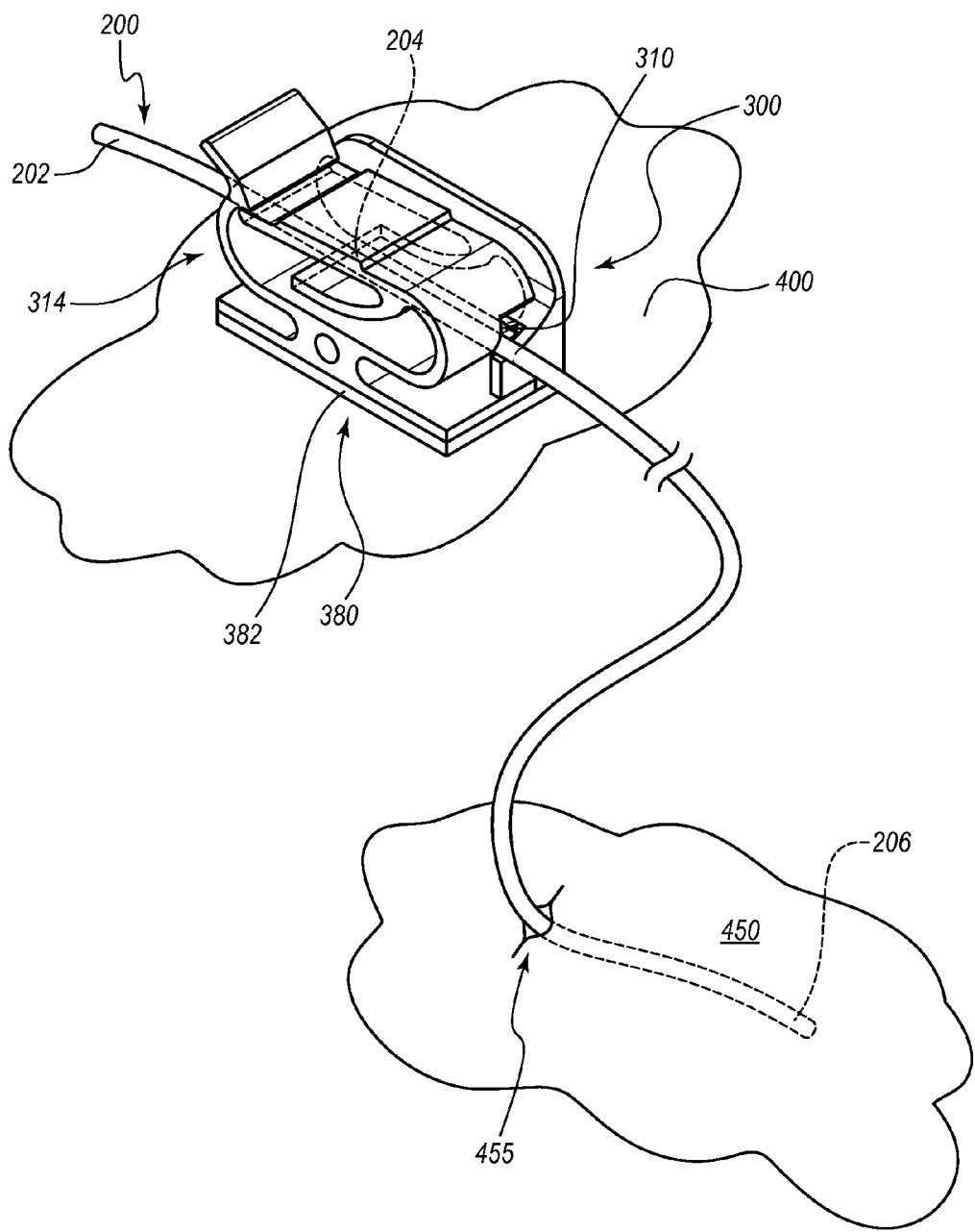
FIG. 10 is a perspective view of the holding device of FIG. 9 that is depicted holding an elongated instrument and being attached to an object such that the device is stationary relative to an insertion site through which the elongated instrument enters a patient.

FIG. 10 is a perspective view of the holding device 300 attached to a separate object 400 via the fastener 380. In the illustrated arrangement, the backing layer 384 has been removed to permit the adhesive layer 382 to be secured directly to the object 400. The object 400 may comprise a portion of a patient 450 or may comprise an object that is distinct from the patient 450. In some arrangements in which the object 400 is distinct from the patient 450, the object 400 can be fixed relative to the patient 450.

The holding device 300 includes a lock 314 that is shown in the closed state. The lock 314 has clamped the intermediate portion 204 of the elongated instrument 200 therein. In such an arrangement, the intermediate portion 204 of the elongated instrument 200 is substantially fixed relative to each of the holding device 300, the separate object 400, and the patient 450.

The proximal end 202 of the elongated instrument 200 is shown extending beyond the holding device 300 in a first direction, and the remainder of the elongated instrument 200 extends from the holding device in a second direction. The elongated instrument 200 enters the patient at an insertion site 455, and the distal end 206 of the elongated instrument 200 is positioned at a desired location within the patient 450.

In some methods of use, the distal end 206 of the elongated instrument 200 is positioned within the patient 450 in any suitable manner. In certain of such embodiments, the proximal end 202 of the elongated instrument 200 may be used in the positioning, such by advancing or retracting the proximal end 202 to effect like movement of the distal end 206 and/or by rotating the proximal end 202 to maneuver the elongated instrument 200 within the patient and/or to provide a torque along a length of the elongated instrument.

In some methods, the holding device 300 is secured to the object 400 before the elongated instrument 200 is positioned as desired within the patient 450. In certain of such embodiments, the elongated instrument 200 is manipulated to move the distal end 206 to the desired position while the elongated instrument 200 is outside of the holding device 300, and the elongated instrument 200 may then be introduced into a channel 310 defined by the device 300. In other embodiments, the elongated instrument 200 may be inserted into a channel 310 defined by the device 300 before the positioning of the distal end 206 is completed. In either case, once the distal end 206 is in the desired position and the elongated instrument 200 is within the channel, the lock 314 may be transitioned to the securing state to prevent movement of the elongated instrument 200 relative to the device 300.

In other methods, the holding device 300 is secured to the object 400 after the distal end 206 of the elongated instrument 200 has been positioned as desired. The elongated instrument 200 may be introduced into the channel 310 before or after the holding device 300 has been secured to the object 400. In either case, once the distal end 206 is in the desired position, the holding device 300 has been secured to the object 400, and the elongated instrument 200 is within the channel, the lock 314 may be transitioned to the securing state to prevent movement of the elongated instrument 200 relative to the device 300.

In some methods, the elongated instrument 200 may be inserted into the device 300 without one or more of the proximal end 202 and the distal end 206 of the elongated instrument 200 passing through any portion of the device 300. For example, in some methods, a practitioner may hold the proximal end 202 of the elongated instrument 200 after having positioned the distal end 206 as desired so as to maintain the distal end 206 in the desired position, and the practitioner may continue to hold the proximal end 202 for this purpose while inserting the elongated instrument 200 into the holding device 300 until the lock 314 has been transitioned to the securing state.

In other embodiments, the fastener 380 is omitted. For example, in some embodiments, the holding device 300 may have a sufficient mass to be immobile relative to a patient when at rest on a surface. The holding device 300 thus may be fixed (e.g., may not move) relative to an immobilized patient due to longitudinal forces and/or residual torques on the elongated instrument 200 that might otherwise cause the elongated instrument 200 to move from a desired position.

The holding device 300 may be used in many suitable contexts. For example, in some embodiments, an individual or discrete holding device 300, such as that depicted in FIGS. 9 and 10, can be used to clamp a single catheter, such as a catheter for a temporary pacemaker. In other embodiments, multiple holding devices may be used together, such as in an assembly. Examples of such multi-holding-device assemblies are discussed below. In some embodiments, the assemblies can advantageously prevent multiple elongated instruments from getting tangled with one another. Other advantages for individual holding devices and holding device assemblies are also contemplated.

Figure 11A:
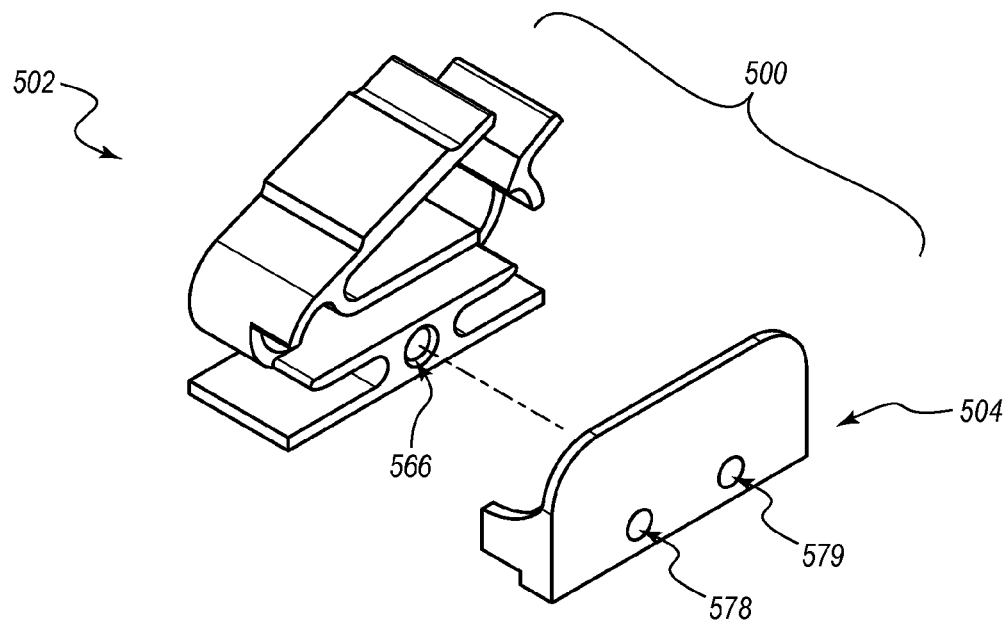
FIG. 11A is an exploded perspective view of another embodiment of a holding device.
Figure 11B:
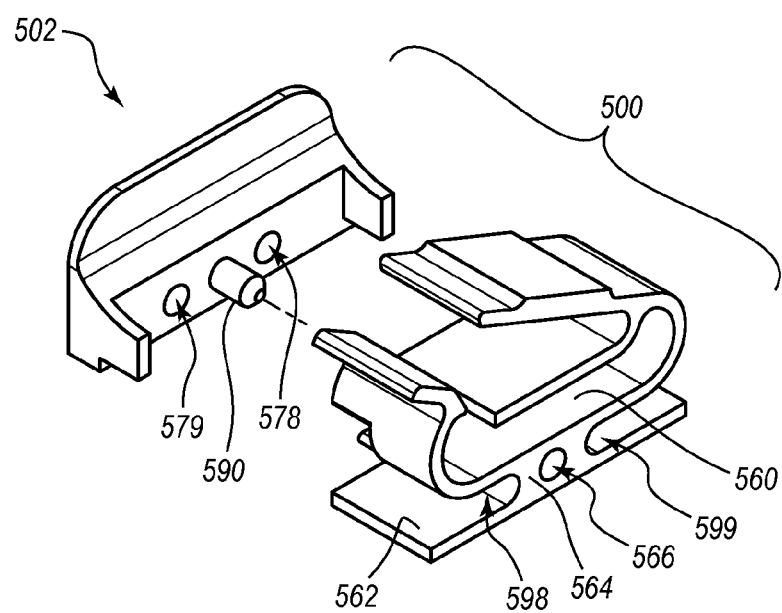
FIG. 11B is another exploded perspective view of the holding device of FIG. 11A.

FIGS. 11A and 11B are exploded perspective views directed generally at opposite faces of another embodiment of a holding device 500 that includes a retaining member 502 and an insertion member 504. The retaining member 502 and the insertion member 504 can include features that facilitate their mutual joining to form a unitary device 500. For example, the retaining member 502 can include a coupling channel 566, which may comprise a bore hole that extends through a full width of the retaining member 502. The insertion member 504 can include a protrusion 590 that is configured to fit snugly in the coupling channel 566. In various embodiments, the retaining member 502 and the insertion member 504 can further be joined together in any suitable manner, such as via one or more of welding, adhesives, etc.

The retaining member 502 and the insertion member 504 can include features that facilitate the joining of multiple holding devices 500 into an assembly of such devices, as discussed further below. For example, the retaining member 502 can define recesses 598, 599 that flank a neck 564. The recesses 598, 599 can be aligned with openings 578, 579 defined by the insertion member 504. Each corresponding set of features can be configured to permit a rail 602 to pass through them, as discussed below with respect to FIG. 12.

Figure 12:
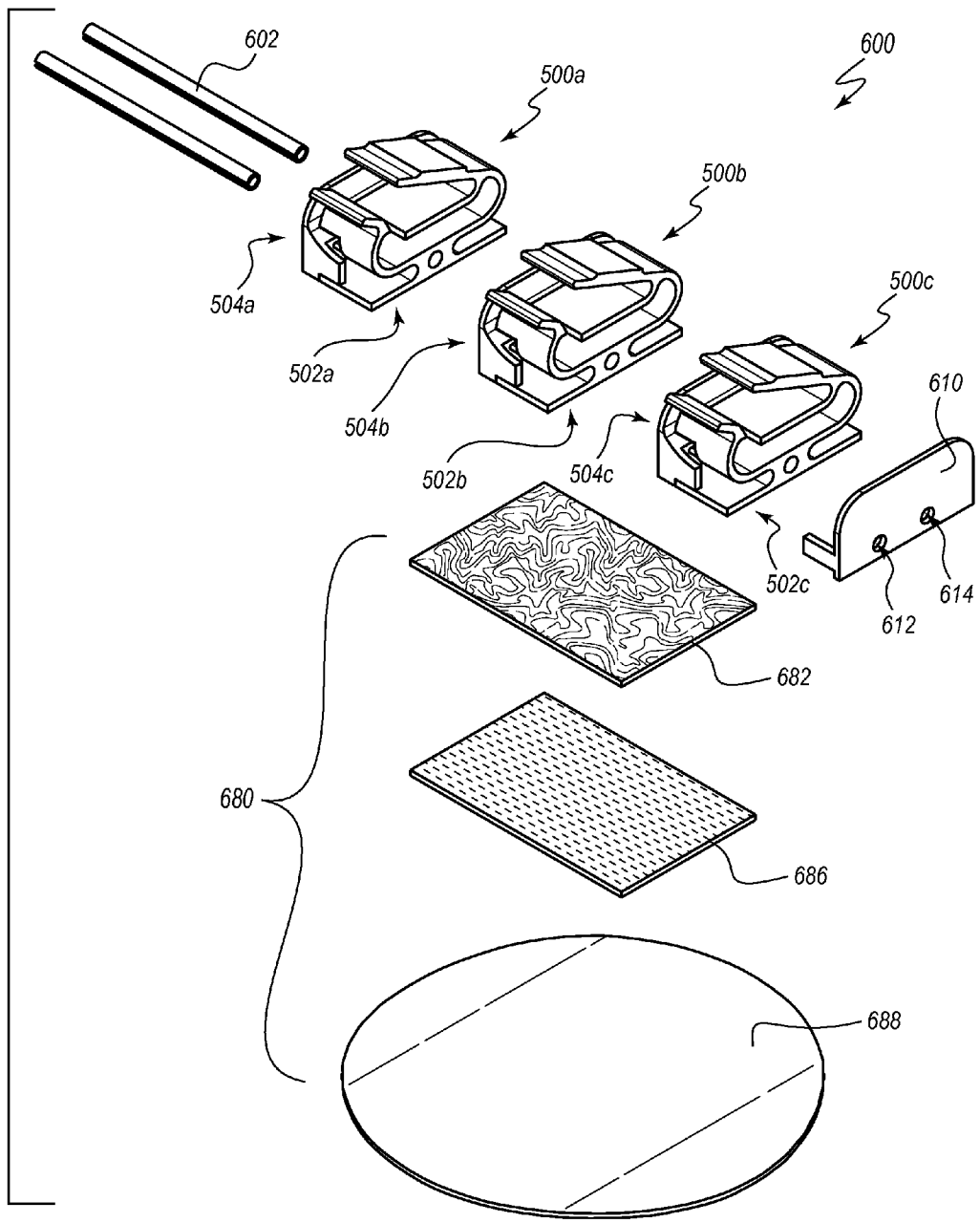
FIG. 12 is an exploded perspective view of an assembly that includes three of the holding devices depicted in FIGS. 11A and 11B.

FIG. 12 is an exploded perspective view of an assembly 600 that includes three holding devices 500a, 500b, 500c, each of which includes a retaining member 502a, 502b, 502c and an insertion member 504a, 504b, 504c. Any other suitable number of devices 500 may be used. The insertion member 504a is positioned at an exterior end of the assembly 600. In some embodiments, a finishing member or an end piece 610 is positioned at an opposite exterior end of the assembly 600. The end piece 610 can define openings 612, 614 through which separate rails 602 may pass.

The holding devices 500a, 500b, 500c may be permanently adhered to an adhesive sheet 682, such as discussed above. In some embodiments, such as that illustrated in FIG. 12, the adhesive sheet 682 may in turn be attached to a hook-and-pile pad 686. A complementary hook-and-pile pad 688 may be configured to selectively engage and disengage the pad 686. The base pad 688 may be configured to be joined to the object 400 discussed above. Together, the pads 688, 686 and the adhesive layer 682 are an embodiment of a fastener 680 that can be used to secure the assembly 600 relative to a patient in any suitable manner. Any other suitable fasteners are possible for the assembly 600, such as those discussed above with respect to the holding device 300. Similarly, in some embodiments, a fastener such as the fastener 680 can be employed with the holding device 300.

Figure 13:
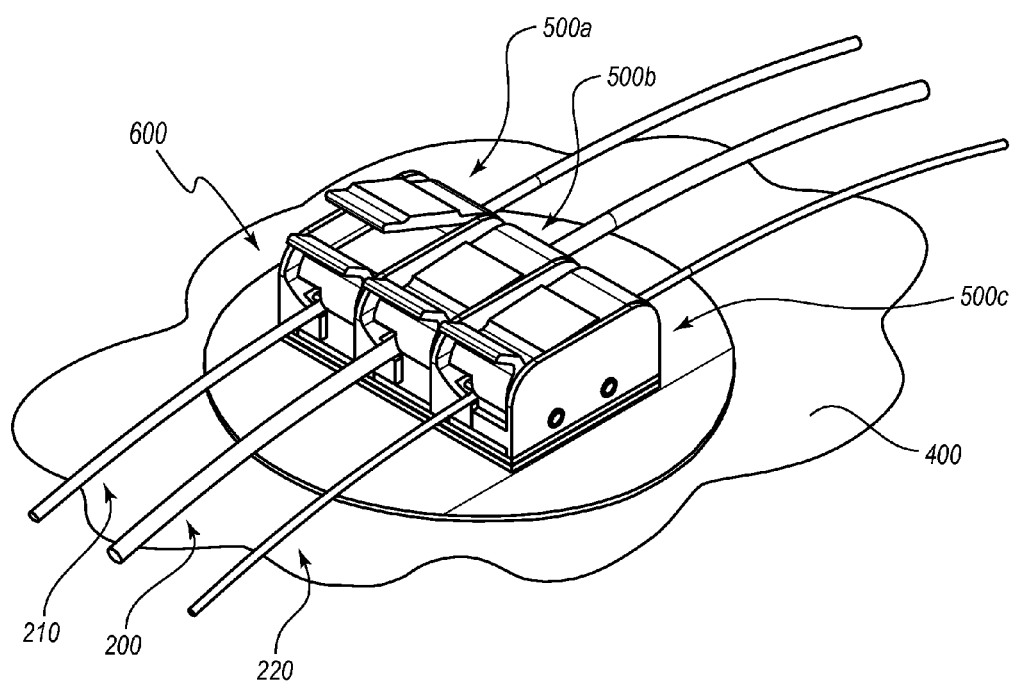
FIG. 13 is a perspective view of the assembly of FIG. 12 attached to an object.

FIG. 13 is a perspective view of the assembly 600 attached to an object. The holding devices 500b, 500c are shown in the securing states, with each holding an elongated instrument 200, 220 having a different diameter. Another elongated instrument 210 is shown having been inserted into the holding device 500a, which is depicted in the open state.

Figure 14:
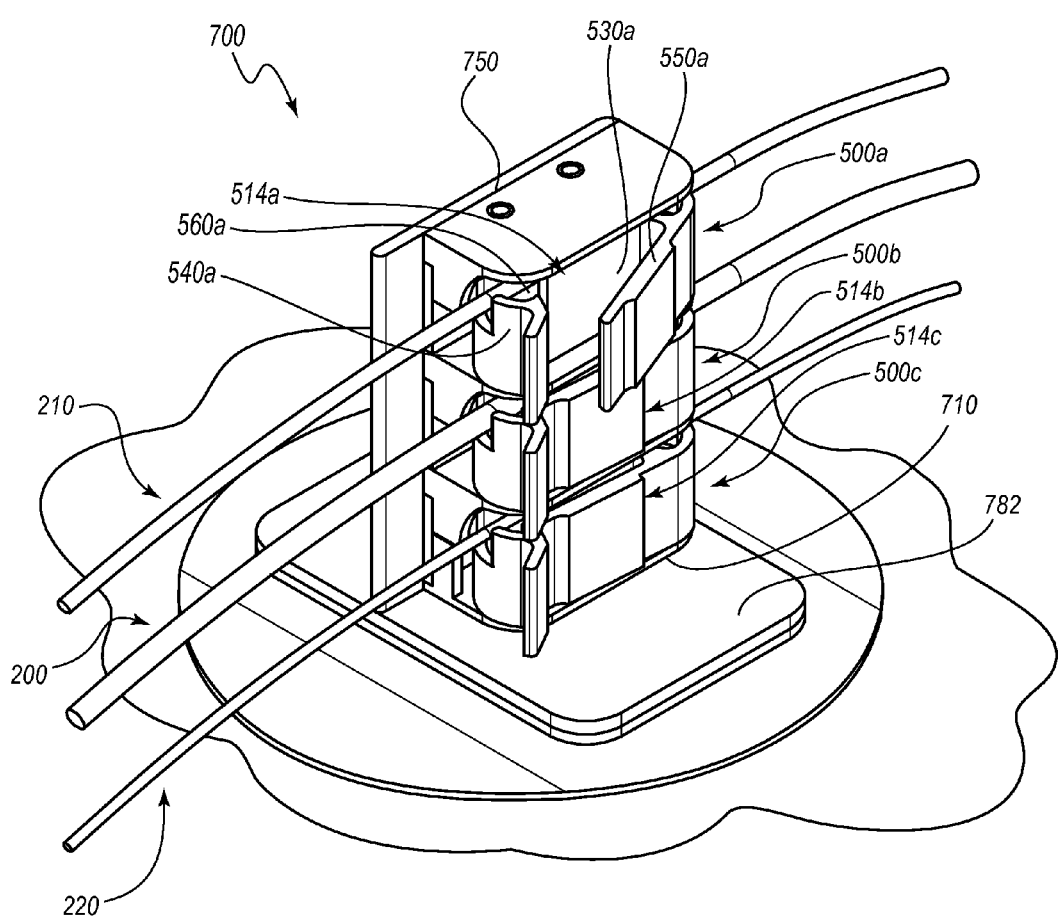
FIG. 14 is a perspective view of another embodiment of an assembly that includes multiple holding devices, wherein the assembly is attached to an object.

FIG. 14 is a perspective view of another embodiment of an assembly 700 that includes multiple holding devices 500a, 500b, 500c. The assembly 700 is attached to the object 400. Rather than a base portion of each of the holding devices 500a, 500b, 500c being secured to an adhesive pad 782, such as with the assembly 600, an end piece 710 is attached to the adhesive pad 782. The holding devices 500a, 500b, 500c extend upwardly from the adhesive pad 782. In some embodiments, a base member 750 is attached to a base of each of the holding devices 500a, 500b, 500c to stabilize the assembly 700.

In some embodiments, the base member 750 can facilitate application of an opposing force during actuation of a lock 514a, 514b, 514c of any of the holding devices 500a, 500b, 500c. For example, the lock 514a can include a locking arm 550a that is configured to be selectively engaged by a latch 540a to transition the holding device 500a between an open state and a securing state, in manners such as discussed above. The lock 514a can further include a spring 530a and a seat 560a that operate in manners such as discussed above with respect to other springs and seats. In moving the locking arm 550a toward the seat 560a to transition the holding device 500a from the open state to the securing state, it may be advantageous to provide an opposing (e.g., oppositely directed) force to an underside of the holding device 500a. In the illustrated embodiment, the base member 750 is positioned at the underside of the holding device 500a, and may conveniently by used to apply the opposing force. Similarly, an opposing force may be applied to a suitable portion of the base member 750 to permit the latch 540a to be moved in a direction that allows the locking arm 550a to be released.

Opposing forces can be applied to opposing sides of other devices described herein to achieve desired actuation of the locks, whether for transitions to or from the locking state. For example, with respect to the holding device 100 depicted in FIGS. 1A and 1B, opposing forces for actuation of the lock 114, whether for transitioning the holding device 100 to the open state or to the securing state, may be applied to one or more suitable portions of an underside of the support 162.

As can be appreciated from the foregoing discussion, in some embodiments, a holding device 100, 300, 500a, 500b, 500c can include a lock that can be actuated in a single action. For example, in some embodiments, a lock (e.g., the lock 114) can be transitioned from the open state to the securing state merely by pushing on a locking arm (e.g., the locking arm 150). In certain of such instances, a latch (e.g., the latch 140) can automatically be deformed as the locking arm is pushed down, and then can elastically rebound to a natural state when the locking arm has been pushed sufficiently far toward a seat (e.g., the seat 160). Thereafter, the latch can continuously engage the locking arm to counteract forces of a spring (e.g., the retention arm 130) and/or a hinge (e.g., the hinge 152) that would otherwise tend to move the locking arm back to the open state. While in the securing state, an intermediate portion of an elongated instrument can be maintained in a fixed position relative to the holding device by the lock.

Similarly, the lock can be actuated in a single action for transition from the securing state to the open state. In some embodiments, the lock (e.g., the lock 114) can be transitioned from the securing state to the open state merely by pushing on the latch (e.g., the latch 140). Such movement of the latch can permit a resilient hinge and/or a resilient spring to urge the locking arm (e.g., the locking locking arm 150) away from the seat (e.g., the seat 160) to open a channel (e.g., the channel 110) and thus permit movement of an elongated instrument within the channel and/or out of the channel.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub routines or only a portion of a method illustrated in the drawings, such as a small subset of step, may be a separate method. Stated otherwise, some additional methods may include only a portion of the steps shown in a more detailed method.

References to approximations are made throughout this specification, such as by use of the terms "substantially," "about" or "approximately." For each such reference, it is to be understood that, in some embodiments, the value, feature, or characteristic may be specified without approximation. For example, where qualifiers such as "substantially," "about" or "approximately" are used, these terms include within their scope the qualified words in the absence of their qualifiers.

Reference throughout this specification to "certain embodiments" or the like means that a particular feature, structure or characteristic described in connection with that embodiment is included in at least some embodiments. However, the quoted phrases, or variations thereof, as recited throughout this specification do not necessarily all refer to the same embodiments.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Recitation in the claims of the term "first" with respect to a feature or element does not necessarily imply the existence of a second or additional such feature or element. Elements specifically recited in means-plus-function format, if any, are intended to be construed in accordance with 35 U.S.C.

§ 112(f). Embodiments of the invention in which an exclusive property or privilege is claimed are defined as follows.

The invention claimed is:

1. A device comprising:
a channel configured to receive therein an intermediate portion of an elongated instrument;
a lock comprising a seat against which the elongated instrument can rest and a resiliently deformable retention arm that is movable relative to the seat, wherein at least a portion of the channel is defined by the seat and the retention arm, and wherein the lock is configured to be selectively transitioned between an open state and a securing state, the retention arm being closer to the seat when the lock is in the securing state, as compared with the open state, wherein the lock further comprises a locking arm that is coupled to the seat via a first hinge, and wherein the retention arm is coupled to the locking arm via a second hinge; and
an insertion path in communication with the channel that is configured to permit the intermediate portion of the elongated instrument to enter the channel when the lock is in the open state without either the proximal end or the distal end of the elongated instrument passing through any portion of the device,
wherein the lock, when in the securing state, is configured to retain within the channel the intermediate portion of the elongated instrument to prevent the intermediate portion from one or more of translating or rotating relative to the device.

2. The device of claim 1, wherein the channel is configured to receive therein an elongated instrument that has a maximum cross-sectional area within a range of different sizes, with a maximum diameter of the cross-sectional area being within a range of from about 0.5 millimeters to about 12 millimeters.

3. The device of claim 1, wherein the retention arm is configured to contact the seat and be loaded thereby when the channel is empty and the lock is in the securing state.

4. The device of claim 1, wherein a distal end the retention arm is moved toward the seat as the lock is transitioned to the securing state, and wherein the distal end of the retention arm is moved away from the seat as the lock is transitioned to the open state.

5. The device of claim 1, wherein the lock further comprises a latch that is configured to be selectively coupled with the retention arm to retain the retention arm in a loaded state, wherein the lock is in the open state when the latch is not coupled with the retention arm, and wherein the lock is in the securing state when the latch is coupled with the retention arm and retains the retention arm in the loaded state.

6. The device of claim 5, wherein the locking arm is configured to directly interact with the latch as the lock is transitioned between the open and the securing states.

7. The device of claim 5, wherein the latch is coupled to the seat via a third hinge.

8. A device comprising:
a channel configured to receive therein an intermediate portion of an elongated instrument;
a lock comprising a seat against which the elongated instrument can rest and a resiliently flexible retention arm that is movable relative to the seat, wherein at least a portion of the channel is defined by the seat, and wherein the lock is configured to transition between an open state and a securing state, the retention arm comprising a distal end that is configured to contact the elongated instrument when the lock is in the securing state, the distal end being moved into proximity to the seat as the lock is transitioned to the securing state and being moved away from the seat as the lock is transitioned to the open state; and
a sidewall, wherein the sidewall defines at least a portion of an insertion path that extends from an insertion opening to the channel, wherein the insertion path is curved;
wherein the channel is capable of receiving the intermediate portion of the elongated instrument when the lock is in the open state, and
wherein the lock, when in the securing state, is configured to retain within the channel the intermediate portion of the elongated instrument to prevent the intermediate portion from moving relative to the device.

9. The device of claim 8, wherein the elongated instrument is gripped by the seat and the retention arm when the lock is in the securing state.

10. The device of claim 8, wherein the retention arm is configured to contact the seat and be loaded thereby when the channel is empty and the lock is in the securing state.

11. The device of claim 8, wherein at least a portion of the retention arm defines at least a portion of the channel.

12. The device of claim 8, wherein the lock further comprises a latch that is configured to be selectively coupled with the retention arm to retain the retention arm in a loaded state, wherein the lock is in the open state when the latch is not coupled with the retention arm, and wherein the lock is in the closed state when the latch is coupled with the retention arm and retains the retention arm in the loaded state.

13. The device of claim 12, wherein the lock further comprises a locking arm to which the retention arm is attached, wherein the locking arm is configured to directly interact with the latch as the lock is transitioned between the open and the securing states.

14. The device of claim 13, wherein the locking arm comprises a first end that is configured to directly interact with the latch and further comprises a second end to which the retention arm is attached via a resilient hinge.

15. The device of claim 8, further comprising a fastener that is configured to secure the device to a separate object.

16. The device of claim 15, wherein the device is configured to prevent longitudinal movement of the elongated instrument relative to an insertion site of a patient at which the elongated instrument enters the patient when the lock is in the securing state and when the device is fixed relative to one or more of (a) the patient or (b) an object that is stationary relative to the patient while the patient is immobile.

17. The device of claim 8, wherein the device is configured to prevent rotational movement of the elongated instrument relative to a longitudinal axis of the elongated instrument when the lock is in the securing state and when the device is fixed relative to one or more of (a) a patient or (b) an object that is stationary relative to the patient while the patient is immobile.

18. The device of claim 8, wherein a ramp extends from the sidewall to the channel, wherein the ramp defines a portion of the insertion path and is configured to facilitate movement of the intermediate portion of the elongated instrument into the channel.

19. The device of claim 8, wherein an entirety of the insertion path is configured to be substantially orthogonal to the intermediate portion of the elongated instrument as the intermediate portion is inserted into the device.

20. The device of claim 19, wherein the intermediate portion of the elongated instrument can be inserted into the device along the insertion path without passing a proximal end or a distal end of the elongated instrument through any portion of the device.

21. A device assembly, comprising:
a first holding device and a second holding device, each holding device comprising:
   a channel configured to receive therein an intermediate portion of an elongated instrument; and
   a lock configured to transition between an open state and a securing state, the lock comprising a resiliently deformable retention arm that is configured to be in a natural state as the intermediate portion of the elongated instrument is received within the channel when the lock is in the open state and is configured to transition to a deformed state by engaging the intermediate portion of the elongated instrument as the lock is transitioned to the securing state;
   wherein the lock, when in the securing state, is configured to retain the intermediate portion of the elongated instrument within the channel and is configured to prevent the intermediate portion of the elongated instrument from one or more of translating or rotating relative to the device;
wherein the device assembly comprises an insertion path that extends from an insertion opening to the channel of the first holding device, wherein the insertion opening is disposed between the lock of the first holding device and the lock of the second holding device.

22. The device assembly of claim 21, wherein each holding device further comprises:
   a sidewall, wherein the sidewall of the first holding device is disposed adjacent the second holding device.

23. The device assembly of claim 21, further comprising a fastener that is configured to secure the device assembly in a fixed position relative to a patient when the patient is immobile.

* * * * *